US010821180B2

(12) United States Patent
Moy

(10) Patent No.: US 10,821,180 B2
(45) Date of Patent: Nov. 3, 2020

(54) DNA REPAIR SKIN CARE COMPOSITION

(71) Applicant: Ronald L. Moy, Beverly Hills, CA (US)

(72) Inventor: Ronald L. Moy, Beverly Hills, CA (US)

(*) Notice: Subject to any disclaimer, the term of this patent is extended or adjusted under 35 U.S.C. 154(b) by 391 days.

(21) Appl. No.: 15/488,305

(22) Filed: Apr. 14, 2017

(65) Prior Publication Data

US 2018/0050103 A1 Feb. 22, 2018

Related U.S. Application Data

(63) Continuation of application No. 13/952,109, filed on Jul. 26, 2013, now abandoned.

(60) Provisional application No. 61/785,231, filed on Mar. 14, 2013, provisional application No. 61/676,268, filed on Jul. 26, 2012, provisional application No. 61/676,262, filed on Jul. 26, 2012.

(51) Int. Cl.
| | |
|---|---|
| *A61K 41/00* | (2020.01) |
| *A61M 37/00* | (2006.01) |
| *A61K 38/18* | (2006.01) |
| *A61K 38/43* | (2006.01) |
| *A61K 9/00* | (2006.01) |
| *A61K 9/127* | (2006.01) |
| *A61K 8/64* | (2006.01) |
| *A61K 8/66* | (2006.01) |
| *A61Q 19/08* | (2006.01) |
| *A61K 8/14* | (2006.01) |

(52) U.S. Cl.
CPC .......... *A61K 41/0047* (2013.01); *A61K 8/14* (2013.01); *A61K 8/64* (2013.01); *A61K 8/66* (2013.01); *A61K 9/0009* (2013.01); *A61K 9/0014* (2013.01); *A61K 9/127* (2013.01); *A61K 38/18* (2013.01); *A61K 38/1808* (2013.01); *A61K 38/43* (2013.01); *A61M 37/0092* (2013.01); *A61Q 19/08* (2013.01); *A61K 2800/82* (2013.01)

(58) Field of Classification Search
None
See application file for complete search history.

(56) References Cited

U.S. PATENT DOCUMENTS

| | | | |
|---|---|---|---|
| 3,211,146 A | 10/1965 | Rodelli | |
| 3,354,884 A | 11/1967 | Rudo | |
| 3,551,554 A | 12/1970 | Herschler et al. | |
| 3,711,602 A | 1/1973 | Herschler et al. | |
| 3,711,606 A | 1/1973 | Herschler et al. | |
| 4,455,256 A | 6/1984 | Urist | |
| 4,557,943 A | 12/1985 | Roster | |
| 4,767,402 A | 8/1988 | Kost et al. | |
| 5,077,211 A | 12/1991 | Yarosh | |
| 5,104,977 A | 4/1992 | Sporn et al. | |
| 5,190,762 A | 3/1993 | Yarosh | |
| 5,272,079 A | 12/1993 | Yarosh | |
| 5,296,231 A | 3/1994 | Yarosh | |
| 5,302,389 A | 4/1994 | Kripke et al. | |
| 5,352,389 A | 10/1994 | Gazzani | |
| 5,352,458 A | 10/1994 | Yarosh | |
| 5,541,170 A | 7/1996 | Rhodes | |
| 5,541,171 A | 7/1996 | Rhodes | |
| 5,618,544 A | 4/1997 | Brown | |
| 5,656,587 A | 8/1997 | Sporn et al. | |
| 5,658,956 A | 8/1997 | Martin et al. | |
| 5,660,836 A | 8/1997 | Knowlton | |
| 5,705,477 A | 1/1998 | Sporn et al. | |
| 5,716,648 A | 2/1998 | Halskov | |
| 5,840,332 A | 11/1998 | Lerner | |
| 5,866,619 A | 11/1999 | Sintov | |
| 6,004,581 A | 12/1999 | Jepsen | |
| 6,023,313 A | 2/2000 | Hazama | |
| 6,030,374 A | 2/2000 | McDaniel | |
| 6,190,315 B1 | 2/2001 | Kost et al. | |
| 6,479,533 B1 | 11/2002 | Yarosh | |
| 6,506,407 B2 | 1/2003 | Watanabe | |
| 6,599,513 B2 | 7/2003 | Deckers et al. | |
| 6,749,624 B2 | 6/2004 | Knowlton | |
| 6,821,524 B2 | 11/2004 | Marini | |
| 7,189,230 B2 | 3/2007 | Knowlton | |
| RE39,573 E | 4/2007 | Von Borstel et al. | |
| 7,320,691 B2 | 1/2008 | Pilcher | |
| 7,834,161 B2 | 11/2010 | Mantyla et al. | |
| 8,221,410 B2 | 7/2012 | Knowlton | |

(Continued)

FOREIGN PATENT DOCUMENTS

| | | |
|---|---|---|
| CN | 106420471 | 2/2017 |
| EP | 0325471 | 7/1989 |

(Continued)

OTHER PUBLICATIONS

"Liposome Technology", edited by G. Gregoriadis, 1984, CRC Press, Boca Raton, Fla. (Chapters 1 and 18) in 17 pages.

(Continued)

*Primary Examiner* — Anand U Desai
(74) *Attorney, Agent, or Firm* — Knobbe, Martens, Olson & Bear, LLP

(57) ABSTRACT

Disclosed is a method of preventing or treating a condition of the gastrointestinal tract. The method includes the steps of providing a DNA repair composition, the DNA repair composition comprising at least one DNA repair enzyme, the DNA repair composition configured for administration within the gastrointestinal tract of a patient; and administering the DNA repair composition to the patient, such that the DNA repair composition is absorbed within the gastrointestinal tract of the patient to treat the condition of the gastrointestinal tract.

12 Claims, 6 Drawing Sheets

Specification includes a Sequence Listing.

(56) References Cited

U.S. PATENT DOCUMENTS

| | | | |
|---|---|---|---|
| 2001/0026807 A1 | 10/2001 | Watts |
| 2001/0036473 A1 | 11/2001 | Scott |
| 2001/0055616 A1 | 12/2001 | Otterbeck |
| 2002/0098235 A1 | 7/2002 | Dittmar |
| 2004/0191197 A1 | 9/2004 | Maio et al. |
| 2004/0236268 A1 | 11/2004 | Mitragotri et al. |
| 2005/0054970 A1 | 3/2005 | Giammarusti |
| 2006/0002884 A1 | 1/2006 | Golz-Berner et al. |
| 2006/0269616 A1 | 11/2006 | Giampapa |
| 2007/0023048 A1 | 2/2007 | Cho |
| 2009/0016971 A1 | 1/2009 | Gaudry et al. |
| 2009/0068255 A1 | 3/2009 | Yu et al. |
| 2010/0151065 A1 | 6/2010 | Courtin |
| 2011/0195112 A1 | 8/2011 | Orvar et al. |
| 2011/0236512 A1 | 9/2011 | Kitazawa et al. |
| 2011/0269693 A1 | 11/2011 | Luebcke |
| 2012/0225029 A1 | 9/2012 | Al-Qahtani |
| 2012/0233798 A1 | 9/2012 | Brewer |
| 2013/0035539 A1 | 2/2013 | Kornstein |
| 2014/0066837 A1 | 3/2014 | Moy |
| 2016/0256375 A1 | 9/2016 | Sanmiguel et al. |

FOREIGN PATENT DOCUMENTS

| | | |
|---|---|---|
| WO | WO 1994/015653 | 7/1994 |
| WO | WO 1998/00194 | 4/1998 |
| WO | WO 2011/008904 | 1/2011 |

OTHER PUBLICATIONS

Carpenter G. and Cohen S (1990), "Epidermal growth Factor", J. Biol. Chen. 265(14):7709-7712.

Fallon, JH et al. (1984) "Epidermal Growth Factor immunoreactive material in the central nervous system: location and development", Science 224(4653): 1107-1109.

Gold MH, Goldman MP, Biron J "Efficacy of novel skin cream containing mixture of human growth factors and cytokines for skin rejuvenation" J Drugs Dermatol. 2007 6(2): 197-201.

Gold MH, Goldman MP, Biron J "Human growth factor and cytokine skin cream for facial skin rejuvenation as assessed by 3D in vivo optical skin imaging" J Drugs Dermatol. 2007 6(10):1018-23.

Lauren Conrad Blog; Sep. 13, 2011; //laurenconrad.com/blog/2011/09/diy-5-step-facial/.

Lautenschläger, Hans "Membrane-containing barrier creams—protecting the skin with skin-related substances" Kosmetische Praxis 2006 (4), 12-14.

M H Barcellos-Hoff "How tissues respond to damage at the cellular level: orchestration by transforming growth factor-β (TGF-β)" British Journal of Radiology Supplement 27 (2005),123-127.

Mehta RC, Fitzpatrick RE "Endogenous growth factors as cosmeceuticals" Dermatol Ther. 2007 20(5):350-9.

Ostro, Marc J., "Liposomes", Scientific American, Jan. 1987, col. 256, pp. 102-111.

Pierce GF et al. "Stimulation of All Epithelial Elements during Skin Regeneration by Keratinocyte Growth Factor" J. Exp. Med. 199479:831-840.

Salib S., et al. "Phonophoresis and the Absorption of Dexamethasone in the Presence of an Occlusive Dressing" Journal of Athletic Training 2007; 42(3):349-354.

Low proteolytic activity in barley background Ref. Dept. of Biochemistry, Science institute, University of Iceland, Reykjavik, Iceland

SEQUENCE LISTING

```
<160> NUMBER OF SEQ ID NOS: 1

<210> SEQ ID NO 1
<211> LENGTH: 43
<212> TYPE: PRT
<213> ORGANISM: Unknown
<220> FEATURE:
<223> OTHER INFORMATION: Epidermal growth factor protein family members.
<220> FEATURE:
<221> NAME/KEY: VARIANT
<222> LOCATION: 2-8, 10-14, 16-28, 30, 32-39, 41
<223> OTHER INFORMATION: xaa = any amino acid
<220> FEATURE:
<221> NAME/KEY: VARIANT
<222> LOCATION: 14, 26-28
<223> OTHER INFORMATION: xaa can either be present or absent.

<400> SEQUENCE: 1

Cys Xaa Xaa Xaa Xaa Xaa Xaa Xaa Cys Xaa Xaa Xaa Xaa Xaa Cys Xaa
1               5                   10                  15

Xaa Xaa Xaa Xaa Xaa Xaa Xaa Xaa Xaa Xaa Xaa Xaa Cys Xaa Cys Xaa
            20                  25                  30

Xaa Xaa Xaa Xaa Xaa Xaa Xaa Gly Xaa Arg Cys
            35                  40
```

DNA REPAIR SKIN CARE COMPOSITION

RELATED APPLICATIONS

This application is related to U.S. application Ser. No. 13/952,109 filed on Jul. 26, 2013, which claims priority under 35 U.S.C, § 119(e) as a nonprovisional application of U.S. Prov. App. No, 61/676,268 filed on Jul. 26, 2012; U.S. Prov. App. No. 61/676,262 filed on Jul. 26, 2012, and U.S. Prov. App. No. 61/785,231 filed on Mar. 14, 2013. The disclosures of each of the foregoing are hereby incorporated by reference in their entireties.

REFERENCE TO SEQUENCE LISTING

The present application includes a Sequence Listing in electronic format. The Sequence Listing is provided as a file entitled MOY005C1SEQUENCELISTING, created Nov. 6, 2017, which is approximately 2 Kb in size. The information in the electronic format of the Sequence Listing is incorporated herein by reference in its entirety.

FIELD OF THE INVENTION

The technology relates generally to compositions and systems for topical application to skin and methods for using and enhancing penetration of the same, and methods for using and enhancing treatment of the body, including the gastrointestinal tract lining.

BACKGROUND OF THE INVENTION

Liposomes can deliver biologically active compounds. DNA repair enzymes and growth factors can repair and protect DNA. Publications discussing liposomes, DNA repair enzymes, and growth factors include: U.S. Pat. Nos. 6,821,524, 6,599,513, 6,479,533, 5,705,477, 5,618,544, 5,656,587, 5,352,458, 5,302,389, 5,296,231, 5,272,079, 5,190,762, 5,104,977, 5,077,211, 4,455,256, and RE39,573; International App. No. PCT/US94/00409; EP Pub. No. EP0325471; J. Exp. Med. 199479:831-840 "Stimulation of All Epithelial Elements during Skin Regeneration by Keratinocyte Growth Factor" by Pierce G E et al.; British Journal of Radiology Supplement 27 (2005), 123-127 "How tissues respond to damage at the cellular level: orchestration by transforming growth factor-$\beta$ (TGF-$\beta$)" by M H Barcellos-Hoff; J Drugs Dermatol, 2007 6(10):1018-23 "Human growth factor and cytokine skin cream for facial skin rejuvenation as assessed by 3D in vivo optical skin imaging" by Gold M H, Goldman M P, Biron J; J Drugs Dermatol. 2007 6(2): 197-201 "Efficacy of novel skin cream containing mixture of human growth factors and cytokines for skin rejuvenation" by Gold M H, Goldman M P, Biron J; and Dermatol Ther. 2007 20(5):350-9 "Endogenous growth factors as cosmeceuticals" by Mehta R C, Fitzpatrick R E. All of the aforementioned patents and publications, as well as all others mentioned in this application, are hereby incorporated by reference in their entireties.

SUMMARY OF THE INVENTION

The technology, in various aspects and embodiments, includes compositions, systems, and methods (e.g., protecting and facilitating healing of biological tissue such as skin damaged by age, environment, medical treatment, and the like) by DNA repair enzymes and growth factors, which can be encapsulated in liposomes, and provide surprising synergistic effects when used in combination. In some embodiments, one or more modalities to significantly increase transdermal penetration of the DNA repair enzymes and/or growth factors are utilized, such as sonophoresis.

In one aspect, the technology includes a skin care composition having one, two, or more growth factors, such as an epidermal growth factor (EGF) and/or keratinocyte growth factor (KGF) for example, a DNA repair enzyme encapsulated by a liposome, and a carrier suitable for topical administration of the growth factor and DNA repair enzyme to a subject's skin.

In another aspect, the technology includes a skin care system having one, two, or more growth factors, e.g., an epidermal growth factor (EGF and/or keratinocyte growth factor (KGF) and a first carrier suitable for topical administration, a DNA repair enzyme encapsulated by a liposome and a second carrier suitable for topical administration, and instructions for topical administration of the growth factor and DNA repair enzyme to the subject's skin.

In still another aspect, the technology includes a skin care method having the steps of topically administering a growth factor, e.g., an epidermal growth factor (EGF) and/or keratinocyte growth factor (KGF) to a subject's skin and topically administering a DNA repair enzyme encapsulated by a liposome to the subject's skin. In some embodiments, the system also includes a sonophoresis device comprising a generator and a transducer, the device configured to increase transdermal absorption of the growth factor and the DNA repair enzyme.

In one aspect, the technology includes a composition having a mixture of liposomes. A first portion of the liposomes encapsulate a DNA repair enzyme and a second portion of the liposomes encapsulate a growth factor.

In another aspect, the technology includes a method including administering liposomes to an individual. A first portion of the liposomes encapsulate a DNA repair enzyme and a second portion of the liposomes encapsulate a growth factor. The liposomes are topically administered to an outer surface of the individual's skin. The DNA repair enzyme and the growth factor are capable of traversing the skin's stratum corneum.

In still another aspect, the technology includes a method for treating skin. The method includes administering a quantity of liposomes to an outer surface of an individual's skin. A portion of the liposomes encapsulate a DNA repair enzyme and a portion of the liposomes encapsulate a growth factor. At least a fraction of the DNA repair enzyme and at least a fraction of the growth factor traverse the skin's stratum corneum such that the fraction of the DNA repair enzyme and the fraction of the growth factor elicit a biological response. In some embodiments, modalities to enhance the absorption of the growth factor and/or the DNA repair enzymes, such as delivery of ultrasonic energy to the skin (sonophoresis), can also be employed.

In various embodiments, the growth factor is EGF. The EGF can be derived from transgenic barley. In certain embodiments, the growth factor is TGF-$\beta$. In some embodiments, the growth factor is KGF, NGF, or another growth factor, several other non-limiting examples of which are disclosed herein.

A biological response can include one or more of repairing DNA, protecting DNA, facilitating healing the skin, rejuvenating the skin, alleviating a symptom associated with the skin, and preventing a skin disorder.

In another embodiment, also disclosed is a skin care composition comprising a growth factor; a DNA repair enzyme encapsulated by a liposome; and a carrier suitable for topical administration of the growth factor and DNA repair enzyme to a subject's skin.

In another embodiment, disclosed herein is a skin care composition comprising a plant-derived recombinant growth factor; a DNA repair enzyme encapsulated by a liposome; and a carrier suitable for topical administration of the recombinant growth factor and the repair enzyme to a subject's skin.

In some embodiments, disclosed herein is a skin care method comprising topically administering a plant-derived recombinant growth factor to a subject's skin; topically administering a DNA repair enzyme encapsulated by a liposome to the subject's skin; and applying ultrasonic energy through the skin surface to increase absorption of the plant-derived growth factor and the DNA repair enzyme, wherein topically administering the growth factor and the DNA repair enzyme are performed under occlusion.

In some embodiments, disclosed herein is a method of preventing or treating a condition of the gastrointestinal tract. The method includes the steps of providing a DNA repair composition, the DNA repair composition comprising at least one DNA repair enzyme, the DNA repair composition configured for administration within the gastrointestinal tract of a patient; and administering the DNA repair composition to the patient, such that the DNA repair composition is absorbed within the gastrointestinal tract of the patient to treat the condition of the gastrointestinal tract. The DNA repair composition can be administered orally, rectally, or by another means. The DNA repair composition can be absorbed, for example and/or configured to act primarily within the oropharynx, esophagus, stomach, small intestine, colon, rectum, or anus of the patient. The DNA repair composition can be pH sensitive in some embodiments. The condition could be, for example, an oropharnygeal ulcer, Barrett's esophagus, peptic ulcer disease, dysplasia of the endothelial lining, a polyp, or inflammatory bowel disease, or carcinoma, among others. In some embodiments, the DNA repair enzyme could be one or more of endonuclease V, O6-methylguanine-DNA methyltransferases, photolyases, uracil- and hypoxanthine-DNA glycosylases, apyrimidinic/apurinic endonucleases, DNA exonucleases, damaged-bases glycosylases, and correndonucleases Also disclosed herein is a therapeutic agent for preventing or treating a condition of the gastrointestinal tract, comprising a DNA repair composition, the DNA repair composition comprising at least one DNA repair enzyme, the DNA repair composition configured for oral administration within the gastrointestinal tract of a patient and configured to be absorbed within the gastrointestinal tract of the patient to effect DNA repair of at least a portion of the lining of the gastrointestinal tract.

The various embodiments described herein can be complimentary and can be combined or used together.

DETAILED DESCRIPTION

Figure 1:
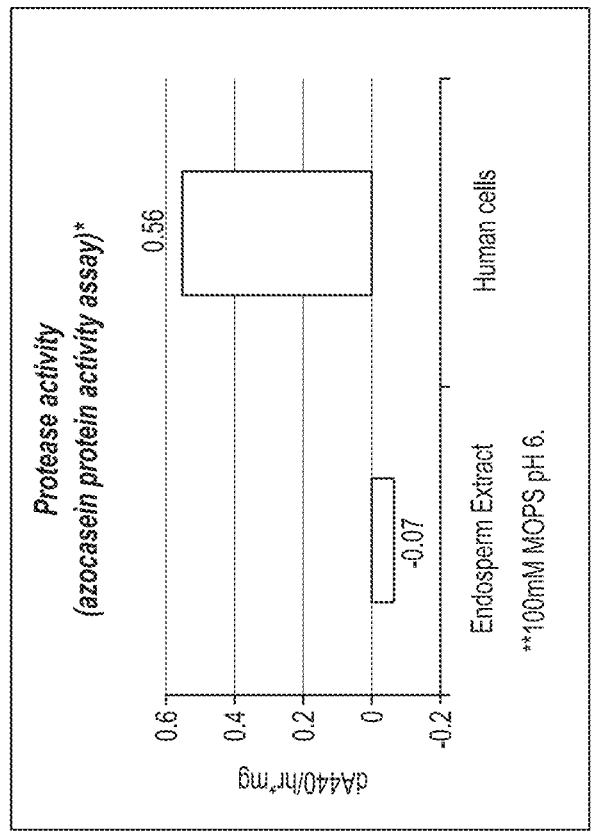
FIG. 1 illustrates a comparison of protease activity of rh-EGF or rh-KGF and recombinant EGF or KGF from *E. coli* or mammalian cells, according to some embodiments of the invention.
Figure 1:
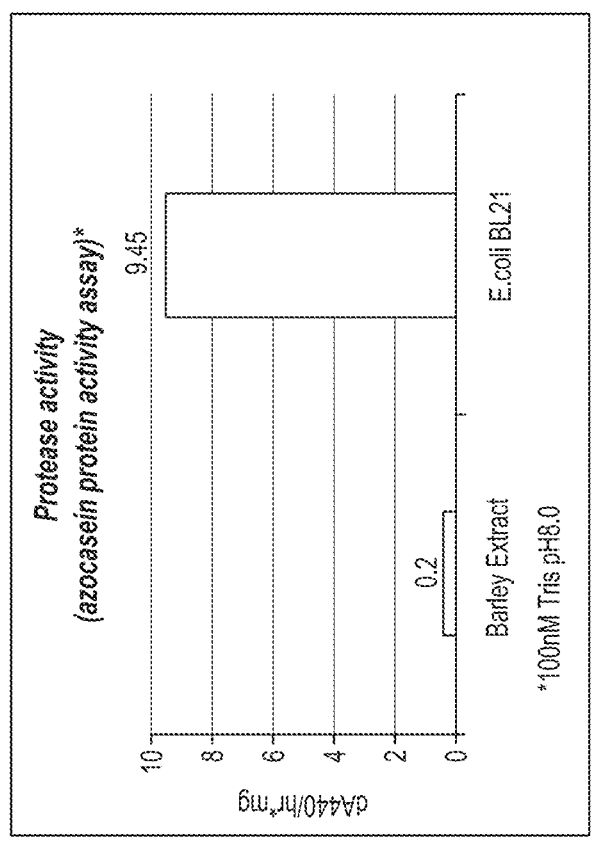

The technology includes skin care compositions, systems, and methods that employ a growth factor (e.g., EGF or KGF, among others), a DNA repair enzyme, or a combination of one or more growth factors and DNA repair enzymes. The growth factor and/or DNA repair enzyme can be encapsulated, either separately or in combination, by liposomes. The compositions and methods can employ a carrier (e.g., a lotion, serum, salve, ointment, gel, cream, cosmetic, preparation, or component thereof) suitable for topical administration to a subject's skin. The growth factor and DNA repair enzyme can be in single or separate carriers. Separate carriers can have the same or different compositions (e.g., each adapted to stabilize and/or facilitate delivery of the included growth factor and DNA repair enzyme).

In one embodiment, the DNA repair enzyme is encapsulated by liposomes while the growth factor is not so encapsulated. In another embodiment, both the DNA repair enzyme and the growth factor are encapsulated by liposomes (e.g., a first portion of the liposomes encapsulate a DNA repair enzyme and a second portion of the liposomes encapsulate a growth factor). In various embodiments, a composition can further include one or more pharmaceutically and/or cosmologically acceptable excipients. In some embodiments, a composition can further include one or more additional DNA repair enzymes and/or growth factors, in certain embodiments, a composition can further include one or more additional therapeutic and/or components (e.g., cosmetic, fragrance, coloring, emollient, preservative, and the like). In various embodiments, a composition can be used for DNA protection and/or repair. DNA can include nuclear and mitochondrial DNA. DNA can be DNA in a skin cell. Protection and/or repair can relate to damage resulting from electromagnetic radiation (e.g., ultra-violet (UV) and X-ray), oxidating and other toxins (e.g., environmental, dietary, pollution, medical such as chemotherapeutics), viral (e.g., herpes virus activation), oncogenic, autoimmune, burns, trauma, diabetic and decubitus ulcers, and the like.

With regard to method of administration, carriers and liposomes used to administer a DNA repair enzyme and/or growth factor can be of various types and can have various compositions. However, carriers and liposomes generally should not be substantially toxic and a liposome generally should be able to deliver at least a portion of its contents into the interior of a cell.

Liposomes can be of various sizes and can have one or more membrane layers separating its internal and external compartments. A liposome can include a sufficient amount of enzyme and/or factor be sequestered so that only one or more liposomes are necessary to enter a cell for delivery of the DNA repair enzyme and/or growth factor. A liposome can be resistant to structural disruption. Liposome structures include small unilamellar vesicles (SUVs, less than 250 angstroms in diameter), large unilamellar vesicles (LUVs, greater than 500 angstroms in diameter), and multilamellar vesicles (MLs). SUVs can be used to administer DNA repair enzymes and/or growth factors. SUVs can be isolated from other liposomes. Enzyme and/or factor an a liposome can be incorporated by molecular sieve chromatography, which can be precise but time consuming and dilutes the liposomes, or differential centrifugation, which can be rapid but produces a wider range of liposome size.

A liposome can include natural and/or synthetic phospholipids, glycolipids, and other lipids and lipid congeners (e.g., cholesterol, cholesterol derivatives, and cholesterol congeners), charged species (e.g., which impart a net charge to the membrane), reactive species (e.g., which can react after liposome formation to link additional molecules to the liposome membrane), and other lipid soluble compounds (e.g., compounds having chemical or biological activity).

A liposome membrane can undergo a phase transition from crystalline to liquid at a temperature ($T_c$) characteristic of the phospholipid composition. When the phospholipid is heated above $T_c$ and then cooled, the membrane can retains water in its amphiphilic lattice and can have one or more characteristics of a gel. To achieve a liquid or gel state, the phospholipid composition should be such that the $T_c$ is lower than the temperature which inactivates the entrapped enzyme and/or factor. Cholesterol in the phospholipid mix can effectively reduce a $T_c$ by broadening a temperature range at which phase transition occurs. One suitable mixture for preparing a liposome includes phosphotidyl choline (or a derivative thereof with a $T_c$ of less than 42° C.), diacetyl phosphate (or a negatively charged species at neutrality), and cholesterol (or a cholesterol derivative). For example, the phosphotidyl choline, diacetyl phosphate, and cholesterol can be at a molar ratio of about 7:2:1.

In some embodiments, pH sensitive liposomes can be used with the technology. Liposomes can enter a cellular cytoplasm by endocytosis into a lysozyme having a low pH. Accordingly, liposomes which are stable at neutral pH but release their contents at acidic pH can be used to deliver enzymes and/or factors into the lysozymes of the cytoplasm, whereupon the contents are released. Since various DNA repair enzymes (e.g., T4 endonuclease V) are relatively stable at low pH, such methods can facilitate delivery of an enzyme into a cell.

Liposomes can be made sensitive to the low pH of the lysozymes by the lipid composition. For example, a pH sensitive liposome can be prepared by using phospholipids that form lipid bilayers when charged but fail to stack in an ordered fashion when neutralized. One such a phospholipid is phosphatidylethanolamine, which is negatively charged above about pH 9. The net charge of a phospholipid can be maintained at a pH which would otherwise neutralize the head groups by including charged molecules in the lipid bilayer which themselves can become neutralized. Such charged molecules include oleic acid, cholesteryl hemisuccinate, and the like, which are negatively charged at about neutral pH but become neutralized at about pH 5, In some embodiments, neutral molecules, such as phosphatidylcholine, can also be added to a liposome where they do not interfere with stabilization of a pH sensitive phospholipid by a charged molecule.

Liposomes including phosphatidylcholine and phosphatidylethanolamine can be more pH sensitive than those of phosphatidylethanolamine alone. In some embodiments, liposomes having a molar ratio of cholesteryl hemisuccinate (CHEMS) to the remaining components of about 1:1 can to respond to pH changes faster than liposomes containing lesser amounts of CHEMS (e.g., minutes versus hours).

Accordingly, in some embodiments, a composition for the pH sensitive liposomes can be phosphatidylethanolamine (PE), phosphatidylcholine (PC), oleic acid (OA), and CLIENTS in a molar ratio of about 2:2:1:5. Various compositions for producing pH sensitive liposomes can be used.

Liposomes can be prepared by combining a phospholipid component with an aqueous component containing the DNA repair enzyme and/or growth factor under conditions resulting in vesicle formation. A phospholipid concentration generally should be sufficient to form a lamellar structure. An aqueous component generally should be compatible with biological stability of an enzyme and/or factor. Methods for combining the phospholipid and aqueous components to form vesicles include: drying a phospholipids onto glass and then dispersing them in an aqueous component; injecting phospholipids dissolved in a vaporizing or non-vaporizing organic solvent into a heated aqueous component; and dissolving phospholipids in an aqueous phase with a detergent and then removing the detergent by dialysis. A concentration of a DNA repair enzyme and/or growth factor in an aqueous component can be increased by lyophilizing the enzyme and/or factor onto a dried phospholipid and then rehydrating the mixture with a reduced volume of aqueous buffer. SUVs can be produced from the foregoing mixtures by methods including sonication and dispersing the mixture through small bore tubing or through a small orifice of a French press.

SUVs/s can be prepared by drying phospholipids onto glass, rehydrating them in aqueous buffer containing a DNA repair enzyme and/or growth factor with shaking at 37° C., sonicating the resulting mixture, and isolating the SUVs containing the DNA repair enzyme and/or growth factor by molecular sieve chromatography and concentrating the SUVs by centrifugation.

A general discussion of liposomes and liposome technology can be found in an article entitled "Liposomes" by Marc J. Ostro, published in SCIENTIFIC AMERICAN, January 1987, volume 256, pages 102-111, and in a three volume work entitled LIPOSOME TECHNOLOGY, edited by G. Gregoriadis, 1984, published by CRC Press, Boca. Raton, Fla.

DNA repair enzymes and/or growth factors incorporated into a carrier and/or liposomes can be administered to living cells internally and/or topically. For internal administration to animals or humans, it is preferable that the liposomes are relatively or substantially pyrogen-free and/or sterile. To eliminate pyrogens, pyrogen-free raw materials, including all chemicals, enzymes, factors, and water, can be used to form the liposomes. Sterilization can be performed by filtration of the liposomes through 0.2 micron filters or by any method known in the art. For injection, the liposomes are suspended in a sterile, pyrogen-free buffer at a physiologically effective concentration. For topical administration, it is preferable that a liposome preparation be relatively or substantially pyrogen-free and/or sterile. Liposomes can be suspended in a carrier material (e.g., buffered polymeric glycol gel) for application to the skin. In some embodiments, a carrier material does not include a non-ionic detergent, which can disrupt a liposome membrane. The concentration of the enzyme and/or factor in the final preparation can vary over a wide range, a typical concentration being on the order of about, at least about, or no more than about 100, 50, 25, 10, 5, 1 or 0.1 µg/ml. In the case of pH sensitive liposomes, lower concentrations of the DNA repair enzyme and/or growth factor can be used, for example, on the order of about 0.001 to 10 µg/ml or about 0.01 to 1.0 µg/ml for liposomes administered to cells internally. In some embodiments, the EGF or KGF can make up between about 1-50%, such as between about 1-25%, 1-10%, 3-8%, or 5-10% of a composition, and be provided in a concentration of at least about 1 ppm, 5 ppm, 10 ppm, 25 ppm, 50 ppm, 100 ppm, 250 ppm, 500 ppm, or more; or no more than about 500 ppm, 250 ppm, 100 ppm, 50 ppm, 25 ppm, 10 ppm, 5 ppm, 1 ppm, or less. In some embodiments, the concentration is between about 25-200 ppm, such as between about 25-100 ppm or 50-100 ppm. Other concentrations can be used if desired.

One method for producing topically applied carriers and/or liposomes encapsulating biologically active proteins is exemplified by the procedure for encapsulation and administration of DNA repair enzymes and/or growth factors. The biologically active protein can be electrophoretically pure. The biologically active protein can be encapsulated under conditions that do not inactivate the protein's biological activity. The concentration of liposomes necessary for topical administration can be determined by measuring a biological effect of the protein in liposomes on target skin cells in culture. Once an active range is found, equal or greater concentrations can be formulated in a composition such as a lotion or gel for application to skin. One example of a dosage range of the final composition for application to the skin is in the range from about 20 to about 100 µl/cm$^2$.

The technology can include the use of a wide range of DNA repair enzymes. A DNA repair enzyme can be from essentially any organism, animal, plant, bacteria, or virus and can be in a pure, extract, or crude form. However, a DNA repair enzyme should be selected to have biological activity despite its origin and/or form.

Bacterial repair systems have been demonstrated to differ significantly from repair in human cells. However, bacterial enzymes such as enzyme endonuclease V (also referred to herein as T4 endonuclease V and den V endonuclease V) have the ability to enhance DNA repair in human cells. Enhanced DNA repair can be evidenced by one or more of increased UV-specific incision of cellular DNA, increased DNA repair replication, and increased UV survival after treatment with the enzyme.

The endonuclease V enzyme can be produced by the denV gene of the bacteriophage T4. T4 endonuclease V can catalyze a rate limiting, first step in the removal of UV-induced DNA damage, namely, single strand incision of DNA at the site of damage. In particular, T4 endonuclease V can exhibit glycosylase and apurinic/apyrimidinic endonuclease activities and can act at the site of ultraviolet induced pyrimidine dimers.

Other enzymes having the ability to repair DNA damage include O6-methylguanine-DNA methyltransferases, photolyases, uracil- and hypoxanthine-DNA glycosylases, apyrimidinic/apurinic endonucleases, DNA exonucleases, damaged-bases glycosylases (e.g., 3-methyladenine-DNA glycosylase), correndonucleases alone or in complexes (e.g., *E. coli* uvrA/uvrB/uvrC endonuclease complex), and other enzymes and enzyme such as, the products of the ERCC genes of humans and the RAD genes of yeast. Generally, a DNA repair enzymes can be enzymes having an ability to participate in repair of any damaged nucleic acid.

*Micrococcus luteus* is one source for a UV-specific DNA endonuclease that has been used for topical application. This DNA repair enzyme has been determined to have the ability to reverse the amount of CPDs in the damaged DNA by localizing in the epidermis and targeting the backbone of the DNA near the dimer. *M. luteus* is a UV-resistant microbe found in marine waters and soil. It has been shown that *M. luteus* removes damaged DNA by stimulating the skin's natural process of DNA damage repair. When the *M. luteus* extract with endonuclease activity is encapsulated in a liposome, it will target the backbone of the DNA near the dimer. It excises the whole portion and synthesizes a new strand in the 5'-3' direction, inserting correct base pairs with their formerly damaged counterparts. The rejoining of the strands is facilitated by polynucleotide ligase. UV-endonuclease speeds natural recovery from sun damage by quickly recognizing sustained damage and targeting those cells. This repair enzyme will enhance correction of UV damage in the skin, as well as prevent future weakening of genetic material, which can cause photoaging and skin cancers. In vitro studies have demonstrated the ability of this enzyme to successfully enhance DNA repair following UV-induced damage, showing that cells treated with this DNA repair enzyme were more likely to survive after being exposed to UV radiation.

The liposome encapsulated *M. luteus* extract (with endonuclease activity) can decrease sensitivity to UV radiation on a reconstituted epidermis with increased sensitivity to UV damage by decreasing the stress on the cells. TNT-α as well as the interleukin isomers released in the cascade following UV exposure will contribute to immune system suppression, but lab tests have shown that their expression can be reduced with the addition of *M. luteus* extract with endonuclease activity. This cytokine cascade causes extraneous protease activity, which will cause the cells to become apoptotic and weakens the structure of the skin. Studies have found a −0.6% decrease in the ability of DNA repair capacity per year as patients aged.

Another example is the OGG-1 repair enzyme, which uses base excision repair to excise 8-oxo-G and repair damage from reactive oxygen species. In base excision repair (BER), one specific base is removed by a glycosylase enzyme, and is replaced with the correct base by DNA polymerase. An encapsulated form of 8-oxo-guanine glycosylase 1 (OGG1) can be used to reverse the damage caused by free radicals. One in vitro study has shown complete removal of 8-oxo-G by OGG1 and therefore repairs of oxidative DNA damage. Furthermore, liposomal delivery of OGG1 into human keratinocytes dramatically increases the rate of 8-oxo-G repair. Topical application of OGG1 can potentially result in decreased tumor size and dramatically reduced tumor progression.

OGG1 can be utilized with a topical delivery system utilizing pH changes43. Once this enzyme is encapsulated in a liposome and applied to the skin, it can penetrate into the epidermis. If the phospholipid encounters a region of changed pH, the liposome will burst and release the enzyme into the cell. Through this method, liposomes are able to penetrate deep into the dermis, where they can be absorbed by the skin and utilized to repair damaged DNA.

Photolyases are another example of DNA repair enzymes. A distinctive source for these enzymes is from the cyanobacteria group Anacytsis nidulans. These proteins contain chromophore cofactors that absorb light, capturing the energy and using it to split CPDs without cleavage of the DNA backbone or involvement of other proteins. This enzyme opens DNA in two different places when repairing it to its original, undamaged state. It has been hypothesized that the splitting of CPDs is achieved through the energy of electron transfer. The photolyase enzyme 'breaks' DNA at two sites and occurs at one site right after another. This separation between break one and two occurs when an electron travels between the two sites. The enzyme inserts an electron into the CPD, and repairs the first site directly, but instead of taking the straightforward path to the second site, the electron takes the circular path around the CPD. There is another molecule that allows the electron to travel more efficiently to the second site, making the indirect pathway more efficient. Topical application of the photolyase lotion reduced the number of UVB-induced cyclobutane dimers by 45% and prevented UVB-induced immunosuppressive effects. In addition, photolyase can prevent erythema and "sunburn" cell formation. Furthermore, CPD repair by photolyase results in upregulation of cytokine-induced intercellular adhesion molecule-1 (ICAM-1) expression in keratinocytes. ICAM-1 stabilizes cell-to-cell interactions and facilitates leukocyte endothelial transmigration. Lastly, photolyase is "photoreactive", meaning that it requires light in order to be activated; therefore it can be a useful adjunct to sunscreens. The visible blue light hits the photolyase and triggers two photoreceptor molecules: FADH and MTHF. These molecules both have the ability to transfer electrons, which is attributed to a theory that photolyases work by the mechanism of electron transfer.

Growth factors are proteins that can bind to receptors on a cell surface. Growth factors can activate cellular proliferation and/or differentiation. Examples of growth factors include EGFs, TGFs, and KGFs.

TABLE 1

Examples of growth factors.

| Factor | Principal Source | Primary Activity | Comments |
| --- | --- | --- | --- |
| PDGF | platelets, endothelial cells, placenta | promotes proliferation of connective tissue, glial and smooth muscle cells | two different protein chains form 3 distinct dimer forms; AA, AB and BB |
| EGF | submaxillary gland, Brunners gland | promotes proliferation of mesenchymal, glial and epithelial cells | |
| TGF-α | common transformed cells | may be important for normal wound healing | related to EGF |
| FGF | wide range of cells; protein is associated with the ECM | promotes proliferation of many cells; induces mesoderm to form in early embryos | at least 19 family members, 4 distinct receptors; has an acid and basic form |
| KGF-1 | Stromal cells | improves reepithelialization after wound healing | Can work qualitatively differently from EGF |
| KGF-2 | Stromal cells | improves reepithelialization after wound healing | |
| NGF | e.g., leukocytes, smooth muscle cells, endothelial cells | promotes neurite outgrowth and neural cell survival | several related proteins first identified as proto-oncogenes; trkA (trackA), trkB, trkC |
| Erythropoietin | kidney | promotes proliferation and differentiation of erythrocytes | |
| TGF-β | activated THI cells (T-helper) and natural killer (NK) cells | anti-inflammatory (suppresses cytokine production and class II MHC expression), promotes wound healing, inhibits macrophage and lymphocyte proliferation | at least 100 different family members |
| IGF-I | primarily liver | promotes proliferation of many cell types | related to IGF-II and pro insulin, also called Somatomedin C |

TABLE 1-continued

Examples of growth factors.

| Factor | Principal Source | Primary Activity | Comments |
| --- | --- | --- | --- |
| IGF-II | variety of cells | promotes proliferation of many cell types primarily of fetal origin | related to IGF-I and pro insulin |

EGF (e.g., epidermal growth factor) is a growth factor that can play a role in the regulation of cell growth, proliferation, and/or differentiation. One example is human EGF. See, for example, Carpenter G and Cohen S. (1990) "Epidermal growth factor" J. Biol. Chem. 265(14):7709-7712. EGF can act by binding to epidermal growth factor receptor (EGFR) on a cell surface and stimulating an intrinsic protein-tyrosine kinase activity of the receptor. Tyrosine kinase activity, in turn, can initiate a signal transduction cascade that results in a variety of biochemical response within the cell. Examples of such biological responses include a rise in intracellular calcium levels, increased glycolysis and protein synthesis, and increases in the expression of certain genes including the gene for EGFR, which can ultimately lead to DNA synthesis and cell proliferation. See, for example, Fallon J H et al. (1984) "Epidermal growth factor immunoreactive material in the central nervous system: location and development" Science 224(4653): 1107-1109.

EGF is one member of an EGF-family of proteins, which can have similar structure and/or function. EGF family members include: Heparin-binding EGF-like growth factor (HB-EGF); transforming growth factor-α (TGF-α); Amphiregulin (AR); Epiregulin (EPR); Epigen; Betacellulin (BTC); neuregulin-1 (NRG1); neuregulin-2 (NRG2); neuregulin-3 (NRG3); and neureguline-4 (NRG4). Family members can include one or more repeats of the conserved amino acid sequence as shown in SEQ ID NO:1. See, for example, Dreux A C et al. (2006) "The epidermal growth factor receptors and their family of ligands: their putative role in atherogenesis" Atherosclerosis 186(1):38-53. Some conserved amino acid sequences can include 6 cysteine residues that can form three intramolecular disulphide bonds, which form three structural loops that facilitate high-affinity binding between members of the EGF-family and their cell-surface receptors. See, for example, Harris R C, Chung E, and Coffey R J. (2003) "EGF receptor ligands" Exp. Cell. Res. 284(1):2-13.

EGF can be used as a therapeutic protein and is commercially available from companies such as Bharat Biotech International of India as REGEN-D®; Daewoong Pharmaceutical of South Korea as EASYEF®; and the Center for Genetic Engineering and Biotechnology of Cuba as CITO-PROT-P®. See, for example, Frew S. et al. (2007) "India's health biotech sector at a crossroads" Nature Biotechnology 25 (4), and Lopez E. et al. (2002) "Development of Cuban Biotechnology" Journal of Commercial Biotechnology 9 (2).

In various embodiments, EGF and/or KGF is derived from transgenic barley. For example, the EGF can be Epidermal growth factor BIOEFFECT™ Serum, recombinant human (CATALOG NUMBER: 03-AA060-0100 available from SIF Cosmetics of Iceland). The recombinant human EGF contains 54 amino acids and a 16 amino acid histidine-based tag, for a total length of 70 amino acid. The recombinant human EGF has a predicted molecular mass of about 8.5 kDa including his-tag and can migrates with an apparent molecular mass of about 12 kDa in SDS-PAGE.

Recombinant human EGF (rh-EGF) or KGF (rh-KGF) can be produced in the endosperm tissue of barley grain (*Hordeum vulgare*). rh-EGF or rh-KGF can exhibit about 50 times less protease activity than recombinant EGF or KGF from *E. coli* or mammalian cells, as shown in FIG. 1. Barley seed extract, among other plant bioreactors, can include other advantages including being void of any human and/or animal viral or other contaminants and including plant-based stabilizing proteins (e.g., dehydrins). In some embodiments, any recombinant growth factor or other component could be derived from a transgenic plant, using, for example, systems and methods described in U.S. Pat. Pub. No. 2011/0195112 A1 to Orvar et al., which is hereby incorporated by reference in its entirety.

Figure 2:
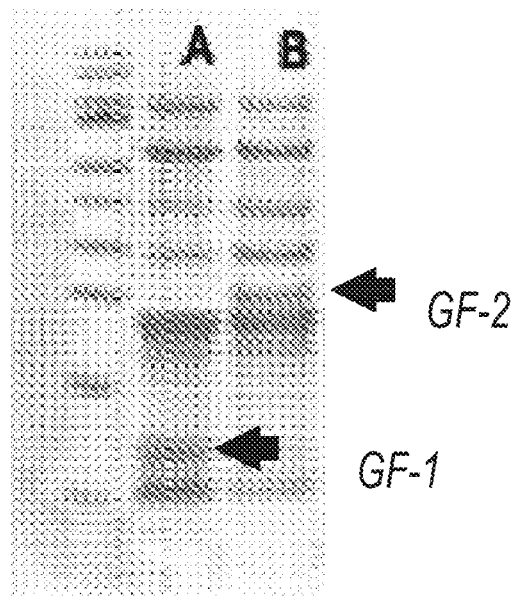
FIG. 2 show electrophoresis results with a single band of two different growth factors and several dehydrin bands, according to some embodiments of the invention.

Recombinant EGF or KGF can be purified from barley grain as an extract that also included dehydrin proteins, which do not interfere with EGF or KGF activity and which can stabilize EGF or KGF. Furthermore, it is hypothesized that dehydrins can enhance the activity of the EGF or KGF, as well as other growth factors and DNA repair enzymes. The image below show one barley grain extract including rh-EGF and dehydrins. Lane A and B of FIG. 2 show electrophoresis results with a single band of two different growth factors and several dehydrin bands.

Figure 3:
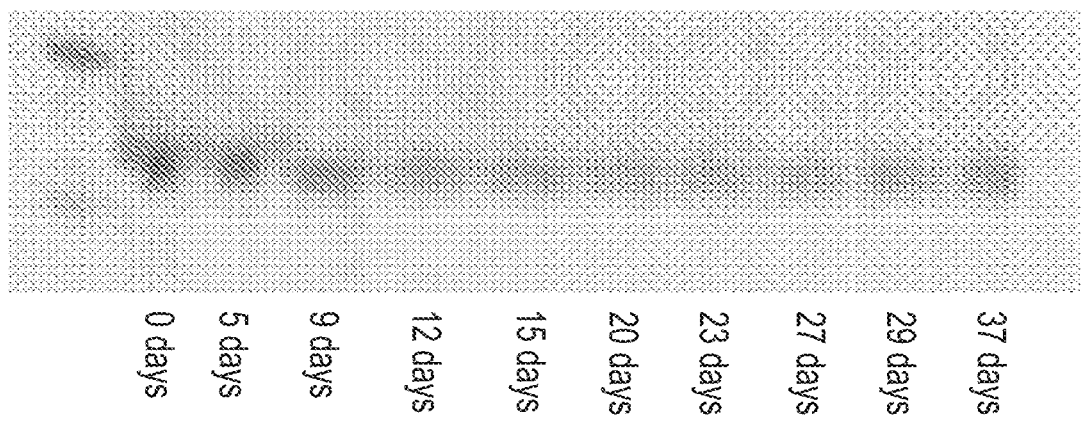
FIG. 3 illustrates an accelerated stability study of rh-EGF or rh-KGF, according to some embodiments of the invention.

Recombinant EGF or KGF from barley can exhibit greater stability than recombinant EGF or KGF from *E. coli* or mammalian cells. For example, rh-EGF or rh-KGF can be stable in a solution at room temperature for at least 12 months. Results from an accelerated stability study are 37° C. are shown in FIG. 3.

Figure 4:
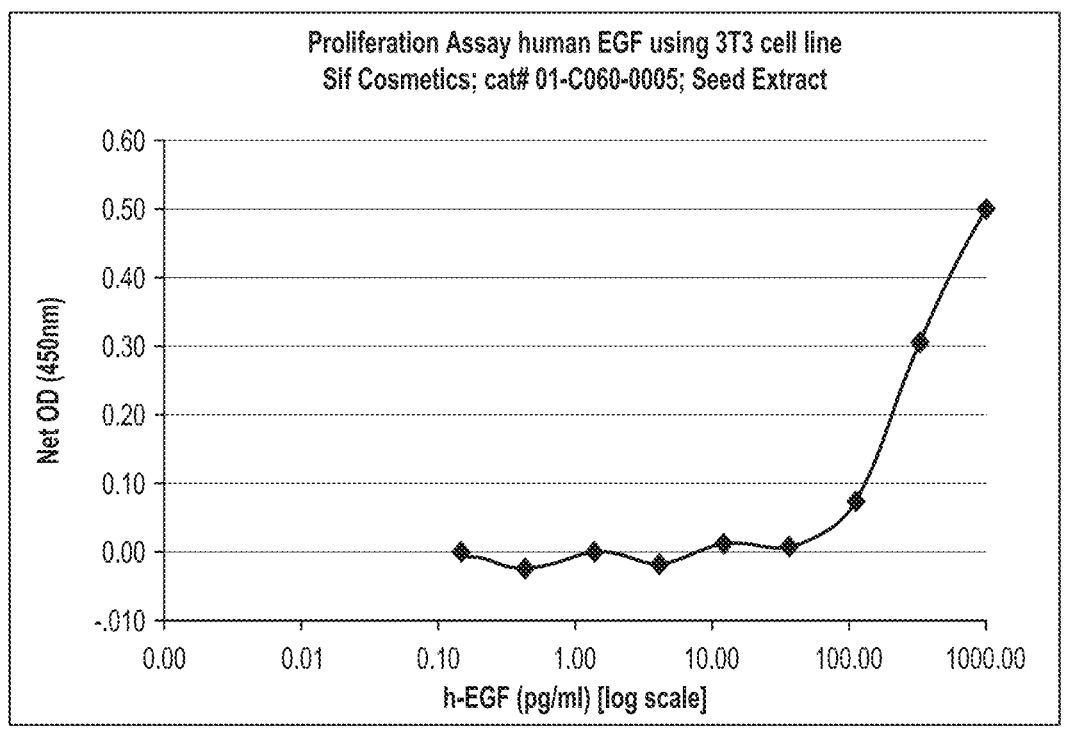
FIG. 4 illustrates that recombinant EGF or KGF from barley can exhibit greater in vitro biological than recombinant EGF or KGF from *E. coli* or mammalian cells, according to some embodiments of the invention.

Recombinant EGF or KGF from barley can exhibit greater in vitro biological than recombinant EGF or KGF from *E. coli* or mammalian cells. In one experiment, rh-EGF bioactivity (as determined by dose dependent effect of human rh-EGF on the proliferation of 3T3 cells) exhibits an EC50 in the range of 0.21-0.32 ng/ml rh-EGF, corresponding to specific activity of $3.1-4.7 \times 10^6$ U/mg, as illustrated in FIG. 4.

Recombinant EGF or KGF from barley can exhibit lower endotoxin levels than recombinant EGF or KGF from *E. coli* or mammalian cells. For example, rh-EGH can have an endotoxin level of less than about 0.005 ng/μg of product (0.05 EU/μg) as measured by a turbidimetric kinetic assay (e.g., Associates of Cape Cod Industries, Deacon Park, Knowsley, Liverpool, UK).

TGF-β (e.g., a transforming growth factor was originally characterized as a protein (secreted from a tumor cell line) capable of inducing a transformed phenotype in non-neoplastic cells in culture. Many proteins homologous to TGF-β have been identified, including TGF-β-1, 2, 3, 4, and 5, which share regions of similar amino acid sequence. The TGF-β-related family of proteins includes the active and inhibit proteins. The Mullein inhibiting substance (MIS) is also a TGF-β-related protein, as are members of the bone morphogenetic protein (BMP) family of bone growth-regulatory factors.

TGF-β can have proliferative effects on many mesenchymal and epithelial cell types. Under certain conditions TGF-β can demonstrate an anti-proliferative effect on endothelial cells, macrophages, and/or T- and B-Lymphocytes. Such effects include decreasing the secretion of immunoglobulin and suppressing hematopoiesis, myogenesis, adipogenesis and adrenal steroidogenesis. Several members of the TGF-β family are potent inducers of mesodermal differentiation in early embryos, in particular TGF-β and activin A.

TGF-α was first identified as a substance secreted from certain tumor cells that, in conjunction with TGF-α-1, could reversibly transform certain types of normal cells in culture. TGF-α can bind to the EGF receptor, as well as its own distinct receptor, and it is this interaction that may be responsible for the growth factor's effect. The predominant sources of TGF-α are carcinomas, but activated macrophages and keratinocytes (and possibly other epithelial cells) also secrete TGF-α. TGF-α can be a potent keratinocyte growth factor.

Keratinocyte Growth Factor (KGF or KGF-1, also known as Fibroblast Growth Factor 7 (FGF-7)) can stimulate the growth of cells in tissues such as the skin and the surface layer of the mouth, stomach, and colon. For example, KGF can maintain a normal structure of skin and/or gastrointestinal surface (lining) and/or can repair skin and/or gastrointestinal lining by stimulating cells to divide, grow, and/or develop. KGF is also present in the epithelialization-phase of wound healing. KGF is an epithelial cell specific mitogen which is secreted by stromal fibroblasts. KGF is a small signaling molecule, having a protein of about 22.5 kDa with a length of 194 amino acids that binds to fibroblast growth factor receptor 2b (FGFR2b). Recombinant human KGF contains 164 amino acids and a 16 amino acid histidine-based tag for a total length of 180 amino acids and has a predicted molecular mass of 21.2 kDa including the his-tag. As a result of glycosylation, the recombinant protein migrates with an apparent molecular mass of 30 kDa in SDS-PAGE. For signaling to occur, a dimer is required between two FGF:FGFR, complexes that are linked together by a molecule of heparin. Not to be limited by theory, but in certain cases, KGF can be as, and in some cases, not more potent than EGF in stimulating proliferation of primary or secondary human keratinocytes. KGF can also result in a very qualitatively different keratinocyte differentiation response than the response in the presence of EGF.

Keratinocyte growth factor-2 (KGF-2), also known as fibroblast growth factor-10 (FGF-10), is a member of the fibroblast growth factor family. KGF-2 is 24 kDa protein having a length of about 215 amino acids, and shares 57 percent sequence homology to previously reported KGF-1 (FGF-7). In skin, both growth factors are expressed in the dermal compartment. KGF-1 and KGF-2 bind to the same receptor with high affinity, the KGFR isoform of FGFR2, which is exclusively expressed by epithelial cells KGF-2 like KGF-1, can lead to significant stimulation of epithelial growth and granulation tissue formation.

In addition to KGF-1 (FGF-7) and KGF-2 (FGF-10), there are about 20 other fibroblast growth factor molecules (FGFs) having a variety of functions including angiogenesis, wound healing, and embryonic development. FGF-1 and FGF-2, for example, stimulate angiogenesis and the proliferation of fibroblasts that give rise to granulation tissue. At least some of the fibroblast growth factors bind to fibroblast growth factor receptors, including FGFR1, FGFR2, FGFR3, and FGFR4. The FGFRs consist of three extracellular immunoglobulin-type domains (D1-D3), a single-span transmembrane domain and an intracellular split tyrosine kinase domain. FGFs interact with the D2 and D3 domains, with the D3 interactions primarily responsible for ligand-binding specificity (see below). Heparan sulfate binding is mediated through the D3 domain. A short stretch of acidic amino acids located between the D1 and D2 domains has auto-inhibitory functions.

Fibroblast growth factor 4 plays a central role during embryonic limb development; in vitro, FGF-4 is mitogenic for fibroblasts and endothelial cells and it has been shown to be a potent angiogenesis promoter in vivo.

Fibroblast growth factor 5 plays a major role during prenatal development and in postnatal growth and regeneration of various tissues, promoting cellular proliferation and differentiation; notably plays a role in the regulation of the hair growth cycle.

Fibroblast growth factor 6 plays a central role in growth and regeneration of a variety of tissues, by promoting cellular proliferation and differentiation; a potent mitogen for fibroblasts, it is important in skeletal muscle regeneration and may have angiogenic activity.

Fibroblast growth factor 8 plays a central role in growth and regeneration of a variety of tissues, by promoting cellular proliferation and differentiation and mediates epithelial-mesenchymal transitions.

Fibroblast growth factor 9 plays a major role during embryonic development and postnatal growth and regeneration of various tissues, promoting cellular proliferation and differentiation.

Heparin-binding EGF-like growth factor signals through the EGF receptor and stimulates the proliferation of smooth muscle cells, fibroblasts, epithelial cells and keratinocytes; produced in monocytes and macrophages. It may play an important role in wound healing.

Interleukin 4 is an anti inflammatory and immunosuppressive cytokine and shows a protective effect towards extracellular matrix degradation. Combination of IL-4 and IL-10 used for treatment of mice with arthritis appeared to markedly protect cartilage destruction.

Interleukin-15 appears to function as a specific maturation factor for NK-cells; stimulates proliferation of the established. T-cell line CTLL-2 and CD80 memory T-cells require IL15 for proliferation.

Noggin is hypothesized to play an important role in the initiation of new hair growth wave in postnatal skin and in apoptosis-driven hair follicle regression in normal skin; exogenous introduction of noggin can restore hair follicle development in lama5(−/−) skin.

Placenta growth factor is a potent angiogenic factors stimulating angiogenesis without significant enhancement of vascular leakage and inflammation; it is expressed during cutaneous wound healing and Improves wound closure by enhancing angiogenesis. Expression of SCF in humans and animals is correlated with the ability of dermal papilla cells inducing hair follicle regeneration. Hair pigmentation is regulated by several factors including the interaction of SCF with its class III receptor tyrosine kinase, c-kit.

lt3 ligand is a ligand for the FLT3 tyrosine kinase receptor and belongs to a small group of growth factors that regulate proliferation of early hematopoietic cells. Multiple isoforms of Flt3 ligand have been identified. Flt3 ligand binds to cells expressing the tyrosine kinase receptor Flt3. Flt3 ligand alone cannot stimulate proliferation, but synergizes well with other CSFs and interleukins to induce growth and differentiation and is therefore suitable addition to compositions containing one or more growth factors.

Other non-limiting examples of growth factors, hormones, proteins, and the like that be included with compositions and methods as disclosed herein include thioredoxin (TRX), stem cell factor (SCF), somatotropin, platelet-derived growth factor (PDGF), vascular endothelial growth factor (VEGF), thymosin-beat-4, and noggin.

Amphoteric hydroxy complexes (AHC) are non-irritating AHAs (alpha-hydroxy acid—glycolic 'sugar' acid) that can be combined with an amino acid for slow, controlled release, and exfoliates the skin, stimulating cell turnover. AHCs can be beneficial to sensitive skin or products formulated for daily use as slow release of the glycolic acid reduces irritation without compromising efficacy. In some embodiments, the AHA may comprise between about 0-10%, 0-5%, about 0-1%, about 1-3%, or about 1-2% of a dermatologic preparation.

Acetyl Tetrapeptide-2 is a highly purified peptide made to mimic the activity of the hormone thymopoietin. It works by reinforcing the cutaneous immune defenses in the skin and also helps stimulate the growth of new cells in the epidermis. In some embodiments, the Acetyl Tetrapeptide-2 may comprise between about 0-10%, 0-5%, about 0-1%, about 1-3%, or about 1-2% of a dermatologic preparation.

*Arabidopsis Thaliana* can effectively reverse oxidative damage to nuclear and mitochondrial DNA in the skin. The DNA repair enzymes from organic sources can help skin repair the effects of exposure to UV rays, environmental pollutants such as ozone, and normal metabolism by the oxidation-intensive mitochondria. In some embodiments, the *Arabidopsis Thaliana* may comprise between about 0-10%, 0-5%, about 0-1%, about 1-3%, or about 1-2% of a dermatologic preparation.

Beta Glucan is derived from oats, and is sub-micron in size, in other words small enough to pass between cells for maximum penetration. Beta Glucan is approved by the FDA and the EU for its skin repair properties. It works by stimulating fibroblasts and is used on surgical implants to speed wound healing. It helps stimulate collagen for added strength to the dermal matrix and provides long term moisturization. In some embodiments, the Beta Glucan may comprise between about 0-10%, 0-5%, about 0-1%, about 1-3%, or about 1-2% of a dermatologic preparation.

*Epilobium Angustifolium* Extract is a botanical extract of willow herb soothes the skin and helps control inflammation. In some embodiments, the *Epilobium Angustifolium* Extract may comprise between about 0-10%. 0-5%, about 0-1%, about 1-3%, or about 1-2% of a dermatologic preparation.

*Hibiscus Abelmoschus* is an active extract enhances the Fibroblast Growth Factor (FGF-2) activity in the skin by mimicking the skin's natural protective function against the deterioration of the extra-cellular matrix. In some embodiments, the *Hibiscus Abelmoschus* may comprise between about 0-10%, 0-5%, about 0-1%, about 1-3%, or about 1-2% of a dermatologic preparation.

Hyaluronic acid is a naturally occurring biopolymer has gained wide use in the medical field for its wound healing properties. Today it is widely used in cosmetic dermatology as the injectable dermal filler of choice and provides exceptional skin hydrating benefits. In some embodiments, the hyaluronic acid may comprise between about 0-10%, 0-5%, about 0-1%, about 1-3%, or about 1-2% of a dermatologic preparation.

Hydroxyproline *Brassica Camprestris* is a moisture barrier repair complex protects the skin against moisture loss and helps prevent future damage. In some embodiments, this complex could comprise between about 0-10%, 0-5%, about 0-1%, about 1-3%, or about 1-2% of a dermatologic preparation.

*Micrococcus* Lysate is an example of a DNA repair enzyme encapsulated in liposomes for improved delivery, and stimulates the skin's natural recovery from sun damage. It is derived from one of the most UV-resistant organisms known to science, found in soil and in the ocean. The enzyme activity stimulates the recognition and elimination of damage to the skin that has been most closely linked to the long-term effects of sun exposure. In some embodiments, the *micrococcus* lysate may comprise between about 0-10%, 0-5%, about 0-1%, about 1-3%, or about 1-2% of a dermatologic preparation.

Monoi Oil, or Monol de Tahiti has been used in Polynesia for centuries to hydrate skin and condition hair. It is made by infusing blossoms from the *Gardenia Taitensis* flower in natural Tahitian coconut oil. This highly emollient oil helps to re-hydrate the layers of the epidermis and shield the skin against the effects of exposure. In some embodiments, the monoi oil may comprise between about 0-10%, 0-5%, about 0-1%, about 1-3%, or about 1-2% of a dermatologic preparation.

Nanopeptide-1 is a skin lightening peptide works to reduce the production of melanin to prevent and lighten hyperpigmentation while restoring an even skin tone. In some embodiments, the nonpeptide-1 may comprise between about 0-10%, 0-5%, about 0-1%, about 1-3%, or about 1-2% of a dermatologic preparation.

*Rosemarinus Officinalis* helps the skin produce the most important components of a healthy lipid barrier to provide added resilience and protection against environmental stressors. In some embodiments, the *Rosemarinus Officinalis* may comprise between about 0-10%, 0-5%, about 0-1%, about 1-3%, or about 1-2% of a dermatologic preparation.

*Salicornia Herbacaea* Extract is a highly refined, ultra-hydrating extract from the coastal marine plant boosts the moisture level in the skin. It has been shown in some cases to increase the water content of the skin by 1000 percent or more. In some embodiments, the *Salicornia Herbacaea* may comprise between about 0-10%, 0-5%, about 0-1%, about 1-3%, or about 1-2% of a dermatologic preparation.

Spanish Lavender is a natural oil that has been shown to reduce the appearance of wrinkles and fine lines as well as inhibit muscle fibers from contracting. In some embodiments, the Spanish lavender may comprise between about 0-10%, 0-5%, about 0-1%, about 1-3%, or about 1-2% of a dermatologic preparation.

Sodium Palmitoyl Proline & Alba Flower is a botanical complex that can soothe the inflammation associated with hyper-pigmentation and age spots. In some embodiments, the complex may comprise between about 0-10%, 0-5%, about 0-1%, about 1-3%, or about 1-2% of a dermatologic preparation.

Vitamins including Vitamins A and E can, alone or in combination, provide the skin with additional antioxidant protection against damage from free radicals. In some embodiments, one, two, or more vitamins may comprise between about 0-10%, 0-5%, about 0-1%, about 1-3%, or about 1-2% of a dermatologic preparation.

The technology can be embodied through various ingredients and methods of preparation. For example, a composition can be in cosmetic and pharmaceutical forms. Such compositions can be for administration for injection, or for oral, pulmonary, nasal, topical, intradermal or transdermal, or other forms of administration.

In one embodiment, the technology can be embodied in a composition for oral administration, which includes at least one DNA repair enzyme encapsulated in a liposome. The composition for oral administration can also include at least one growth factor, optionally encapsulated in a liposome. The composition can be adapted to deliver a DNA repair enzyme, a growth factor, or both to the gut (e.g., anyone or more portions of the gastrointestinal tract after the stomach). For example, the composition can include one or more enteric coatings, encapsulations, or other suitable formulations, to deliver the a DNA repair enzyme, a growth factor, or both in an active form to the gut.

The synergistic combination of at least one growth factor, such as EGF and/or KGF for example, and at least one DNA repair enzyme can advantageously prevent or treat a wide variety of conditions, including dermatologic conditions that can, in some embodiments, improve the condition of the skin to a greater degree than the combined effect of either the growth factor or the DNA repair enzyme alone. Not to be limited by theory, the DNA repair enzyme removes damaged DNA and stimulates generation of normal DNA, while the growth factor accelerates the proliferation of healthy skin cells.

Compositions can include a mixture of liposomes, a first portion of the liposomes encapsulating a DNA repair enzyme and a second portion of the liposomes encapsulating a growth factor, together with cosmetic or pharmaceutically acceptable diluents, preservatives, solubilizers, emulsifiers, adjuvants, and/or carriers. Such compositions can include diluents of various buffer content (e.g., Tris-HCI, acetate, phosphate), pH and ionic strength; additives such as detergents and solubilizing agents (e.g., polysorbates such as Polysorbate 80, which is sold as TWEEN 80®), moisturizing agents (e.g. ceramides, alpha-hydroxy acids), anti-oxidants (e.g., ascorbic acid, sodium metabisulfite), preservatives (e.g., phenoxyethanol, phenonip, thimerosal, benzyl alcohol), and bulking substances (e.g., lactose, mannitol). Hyaluronic acid can also be used. Such compositions can influence the physical state, stability, rate of in vivo release, and rate of in vivo clearance of a DNA repair enzyme and a growth factor. Compositions can be prepared in liquid or lotion form, or can be in dried powder, such as lyophilized form, or can be prepared as a spray or aerosol.

In some embodiments, the product can have a pH of about 7.03±0.2 and a viscosity of about LV T-E at 0.3 rpm 498,400 cps±10%.

A product produced by a method can be packaged in a container. For example, a product can be packaged in a tube, bottle, spray, pump, or other container suitable for a consumer. A product can also be packaged in a tank or vat for transportation or distribution (e.g., packaged for a consumer later). The container can be any glass, metal, plastic, or other material suitable for a consumer or commercial market.

In various embodiments, methods can be adapted to prepare compositions according to the technology. In some embodiments, group 5 ingredients include EGF, TGF-β, and/or KGF. In such embodiments, group 1-4 ingredients can include any combination of ingredients, excipients, or the like for compositions such as a lotion, ointment, salve, paste, cream, spray, balm, gel, liquid or the like.

In various embodiments, a composition can optionally include an ingredient that can repair UV damage and reduce the expression of TNFα and IL-10, for example, a *micrococcus* lysate and lecithin such as ULTRASOMES® (AGI Dermatics of Freeport, N.Y.).

The extract can prepared from a UV-resistant organism and encapsulated in liposomes such as liposomes including lecithin. In some embodiments the liposomes are dispersible in water and have a pH range of about 7.5-8.5. The liposomes including micrococcus lysate can be used at about 0-5% or about 1%. The liposomes including micrococcus lysate can be added to the composition at a temperature of about 45° C. or lower. Note that ULTRASOMES® may be incompatible with 5% ethylene glycol, 5% glycerin, alcohol, anionics, ionic detergents, or surfactants.

In some embodiments, a composition can optionally include an ingredient that can absorb visible light to cleave and reverse damage caused by shorter wave length UV (e.g., reduce sunburn), for example, a plankton extract and lecithin such as PHOTOSOMES® (AGI Dermatics of Freeport, N.Y.). The cell extract derived from ocean plankton can be activated by visible wavelengths of sunlight and can be packaged in liposomes such as lecithin containing liposomes. The liposomes containing the cell extract derived from ocean plankton can be dispersible in water and have a pH range of about 7.5-8.5. The liposomes containing the cell extract derived from ocean plankton can be used at about 0-5% or about 1%. The liposomes containing the cell extract derived from ocean plankton can be added to the composition at a temperature of about 45° C. or lower. Note that PHOTOSOMES® may be incompatible with 5% ethylene glycol, 5% glycerin, alcohol, anionics, ionic detergents, or surfactants.

In certain embodiments, a composition can optionally include an ingredient that can repair oxidative DNA damage, for example, an *Arabidopsis thaliana* extract and lecithin such as ROXISOMES® (AGI Dermatics of Freeport, N.Y.). The plant enzyme that repairs oxidative damage can be encapsulated in liposomes such as lecithin containing liposomes. The liposomes containing the plant enzyme can be dispersible in water and have a pH range of about 7.5-8.5. The liposomes containing the plant enzyme can be used at about 0-5% or about 0.3-1.0%. The liposomes containing the plant enzyme can be added to the composition at a temperature of about 40° C. or lower.

In various embodiments, a composition can optionally include an ingredient that is designed to counteract the signs of biological and UV induced premature skin aging, help to reduce UV-induced DNA damage, prevents the release of ECM-decomposing proteases, and improve skin firmness, for example, a water and glycerin and glycine soja (e.g., soybean) seed extract such as PHYTOSAN™ by CUR Chemisches Laboratorium GmbH of Berlin, Germany. PHYTOSAN™ is water soluble. PHYTOSAN™ can be used at about 0-10% or about 2-5%.

In some embodiments, a composition can optionally include an ingredient that can have a neuroprotection, anti-stress, and anti-apoptotic effect, for example, a glutamylanidoethyl indole and water such as GLISTIN® (Exsymol of Monaco). The glutamylanidoethyl indole and water can be water soluble and can be used at about 0-5% or about 1%.

In various embodiments, a composition can optionally include an ingredient that can be a cell energizer, protect DNA from various aggressors, stimulates protein synthesis (e.g., keratin, filaggrin, collagen, fibronectin), and cellular revitalizer, for example, a water and Artemia Extract such as GP4G® (MMP, Inc. of South Plainfield, N.J.). The Anemia Extract can be water soluble. The Artemia Extract can be used at about 0-10% or about 1-5%. The Artemia Extract can be added to the composition at a temperature of about 40° C. or lower.

In various embodiments, a composition can optionally include an ingredient that counteracts the protein oxidative cross-linking, reduces and detoxifies membrane hydroperoxides, for example, a Decarboxy Carnosine HCI such as ALISTIN® (Exsymol Monaco). Decarboxy Carnosine HCI can be water soluble. Decarboxy Carnosine HCI can be used at about 0-20% or about 0.5-15%.

In some embodiments, a composition can optionally include an ingredient that activates SIRTI expression in human skin, increases cellular longevity, increases skin repair and protection, and increases DNA protection from UV stress and peroxide stress, for example, a water and glycerin and *Oryza sativa* (e.g., rice) extract such as ORSIRTINE™ (ISP Vincience of Sophia Antipolis, France). The *Oryza sativa* extract can be water soluble. The *Oryza sativa* extract can be used at about 0-5% or about 1%.

In certain embodiments, a composition can optionally include an ingredient that preserves skin from oxidative stress, improves the natural defense mechanisms against oxidative stress (e.g., SOD and catalase), improves DNA protection, reduces protein carbonylation, decreases lipid peroxidation, and protects against glycation damage, for example, a einkom (*triticum monococcum*) extract such as PHYTOQUINTESINE™ (ISP Vincience of Sophia Antipolis, France). The einkorn can be water soluble. The einkorn can be used at about 0-20% or about 0.5-15% or about 1-5%.

In some embodiments, a composition can optionally include one or more of the following active agents, either alone or in combination: Vitamin C; Vitamin D; Vitamin E; Vitamin A; Vitamin K; Vitamin F; any of the various chemical forms and analogues of these vitamins; Retin-A (Tretinoin); Adapalene; Retinol; Hydroquinone; Kojic acid; various growth factors; echinacea; antibiotics; antifungals; antivirals; bleaching agents: alpha hydroxy acids; beta hydroxy acids; salicylic acid; antioxidant triad compound (with or without Tretinoin or Vitamin A derivatives); seaweed and salt water derived products antioxidants, phytoanthocyanims, phytonutrients, botanical and herbaceous products, hormones (including insulin or estrogens), enzymes, minerals, growth factors, genetically engineered substances, cofactors or catalysts for various biological pathways and other antiaging substances.

In some embodiments, a scar cream preparation can be utilized. In some embodiments, the scar cream preparation can include, for example, citric acid, SymWhite, Lexfeel D5, SymPeptide 222, SymGlucan, Chlorellagen D P, PhykoAIPF, BMX Complex, Lupinol-47, and/or soline.

In some embodiments, a growth factor preparation can be utilized. The growth factor preparation can include between about 1-50 ppm of EGF and/or KGF, such as about 1 ppm, 2 ppm, 5 ppm, 10 ppm, 15 ppm, 20 ppm, 25 ppm, 30 ppm, 35 ppm, 40 ppm, 45 ppm, or 50 ppm (for a final growth factor content of between about 1-10 ppm, about 1 ppm, about 2 ppm, about 5 ppm, or about 10 ppm).

In some embodiments, an eye cream preparation can be utilized. Not to be limited by theory, the eye preparation (also referred to herein as an eye renewal preparation, to be applied to eyelids and periorbital skin) includes DNA repair enzymes to counteract general skin decline and replenish the apply of naturally-occurring DNA repair enzymes. Beta glucans can strengthen the periorbital skin matrix via 3-dimensional collagen growth. *Rosemarinus officinalis*, hyaluronic acid, and willowherb can reprogram the production of lipids and strengthen, rehydrate, and reduce inflammation. Spanish lavender and matrixyl 3000 can inhibit natural muscle contractions and target deep wrinkles (such as crow's feet). Tetrapeptides can diminish the appearance of dark circles, skin thinning, and wrinkles.

In some embodiments, an intensive renewal preparation can be utilized. Not to be limited by theory, *Hibiscus* peptides and DNA repair enzymes can enhance cell turnover and restore skin vitality, as well as repair negative photodamage responses and initiate cellular repair mechanisms. *Salicornia Herbacea* Extract and Rapeseed Sterol can be used to retain moisture and restore the skin's natural lipid barrier. Nonopeptide-1 and/or alba flower, among other components, can counter UV-inducted damage, prevent pigmentation and age spots.

In some embodiments, a night cream preparation can be utilized. Not to be limited by theory, the night preparation (also referred to herein as a night renewal preparation)

includes DNA repair enzymes, that when applied nocturnally, can maximize cell repair activity during the body's sleep cycle. High levels of DNA repair enzymes, peptides, and botanical actives can restore dry, damaged skin within weeks. *Rosemarinus officinalis*, hyaluronic acid, and willowherb can reprogram the production of lipids and strengthen, rehydrate, and reduce inflammation. Spanish lavender and tetrapeptides can prevent or treat the formation of age spots, skin thinning, and wrinkles.

In some embodiments, a renewal foaming cleanser can be utilized. Not to be limited by theory, the instant foam produced from a naturally-derived sulfate-free cleansing agent can completely dissolve makeup, oils, and impurities. The amino acid glycoic complex (AHC) can stimulate cell turnover and wash away damaged epithelial cells to prime skin for maximum regeneration. The cleansing agent can be advantageously free of artificial fragrances, sulfates, and parabens.

fraction of the DNA repair enzyme and the fraction of the growth factor elicit a biological response. Generally, a biological response can include activating, inhibiting, accelerating, amplifying, extending, facilitating, and/or effecting any biochemical pathway or reaction. For example, a biological response can include one or more of: repairing DNA, protecting DNA, increasing collagen and or elastin expression, facilitating curing the skin, healing the skin, rejuvenating the skin, alleviating a symptom associated with the skin, and preventing a skin disorder. Rejuvenating the skin can include one or more of mitigating wrinkles, tightening skin, and mitigating discoloration and/or age spots.

Example 1

Protocols

TABLE 2

Treatment protocols.

| Product | Use | | Function | | | | | Feature | |
|---|---|---|---|---|---|---|---|---|---|
| | AM | PM | Renew | Repair | Hydrate | Cleanse | Protect | EGF/KGF | DNA Repair |
| Growth Factor Preparation | | ✓ | ✓ | ✓ | | | | ✓ | |
| Intensive Renewal Preparation | ✓ | ✓ | ✓ | ✓ | ✓ | | | | ✓ |
| Night Preparation | | ✓ | ✓ | ✓ | ✓ | | | | ✓ |
| Eye Preparation | ✓ | ✓ | ✓ | ✓ | ✓ | | | | ✓ |
| Cleanser | ✓ | ✓ | | | ✓ | ✓ | | | |
| Sunscreen | ✓ | | | | | | ✓ | | |

Sunscreen preparations can prevent solar damage from UV and other solar radiation. In some embodiments, a sunscreen preparation could include one or more of the following components: Ethylhexyl Methoxycinnamate, Oxybenzone, Zinc Oxide, Phenylbenzamidazole Sulfonic Acid, Water, Isononyl Isononanoate, C12-15 Alkyl Benzoate, Glycerin, Cyclomethicone, Cetearyl Alcohol, Ceteareth-20, Octyldodecyl Neopentanoate, Butylene Glycol, Dicetyl Phosphate, Ceteth-10, Phosphate, Magnesium Aluminum Silicate, Retinyl Palmitate, Tocopheryl Acetate, Dimethicone, Xanthan Gum, PVP/Eicosene Copolymer, Tetrasodium EDTA, Potassium Hydroxide, Triethxycaprylylsilane, Caprylyl Glycol, Phenoxyethanol, Hexylene Glycol.

The technology includes various methods of administering compositions.

One method according to the technology includes administering liposomes to an individual, wherein a first portion of the liposomes encapsulate a DNA repair enzyme and a second portion of the liposomes encapsulate a growth factor, wherein the liposomes are topically administered to an outer surface of the individual's skin, and wherein the DNA repair enzyme and the growth factor are capable of traversing the skin's stratum corneum.

In various embodiments, a method for treating skin includes administering a quantity of liposomes to an outer surface of an individual's skin. A portion of the liposomes encapsulate a DNA repair enzyme and a portion of the liposomes encapsulate a growth factor. At least a fraction of the DNA repair enzyme and at least a fraction of the growth factor traverse the skin's stratum corneum such that the Table 2 shows a number of non-limiting potential treatment protocols, together with the respective use time, function, and features of various preparations. In various embodiments, a growth factor preparation, e.g., an EGF and/or KGF containing preparation (e.g., the Growth Factor Preparation of example 2) is applied in the evening, in combination with at least one DNA repair enzyme containing preparation (e.g., the Intensive Renewal Preparation, Night Preparation, and/or Eye Preparation of examples 4, 3, and/or 5, respectively). In some embodiments, the growth factor preparation is used daily until the desired results are achieved, and then 2 to 3 times weekly to maintain skin radiance. In some embodiments, a treatment protocol also includes applying at least one DNA repair enzyme containing preparation in the morning. In certain embodiments, the DNA repair enzyme can be a UV light activated DNA repair enzyme. A treatment protocol can include the use of a hydrating skin cleanser in the evening and/or morning. A treatment protocol can also include the use of a sunscreen (e.g., SPF 30+), such as following the morning regimen to prevent further sun damage. The sunscreen, in some embodiments, includes zinc oxide, such as micro-fine zinc oxide, to reflect and scatter UV light; and Vitamins A and E to promote dermal matrix protection and anti-oxidant activity. In some embodiments, such treatment protocols can be used, for example, to treat fine lines and wrinkles (e.g., to promote skin thickening and/or tightening), uneven skin tone and discoloration, under eye circles and swelling, photodamage, acne-prone skin and enlarged pores, sensitive skin, and rosacea. In some embodiments, one or more dermatologic conditions that can be treated include a malignant condition such as a skin cancer, including melanoma, basal cell carcinoma, or squamous cell carcinoma. The dermatologic condition could predispose a patient to a greater risk of developing skin cancer, the condition includes one or more such as actinic keratosis, xeroderma pigmentosum, or albinism, for example. A wide variety of other dermatologic conditions, including but not limited to bruising or senile purpura, burns, age spots, sun spots, scars including keloids, eye bags, xerosis, ichtyosis, keratoderma, dermatofibroma, dermatitis, acne, neurodermatitis, dermatitis herpetiformis, vitiligo, vasculitis, pemphigus, bullous pemphigoid, hyperkeratosis, eczema, psoriasis, rosacea, pityriasis rosea, warts; bacterial, viral, fungal, or other infections can also be also potentially treated using the systems, preparations, and methods as disclosed herein, in some embodiments, the dermatologic condition to be treated could be a manifestation of a systemic disease, such as an autoimmune disease such as systemic lupus erythematosus, scleroderma, or rheumatoid arthritis, for example. In some embodiments, preparations and methods herein can be utilized for the treatment of unwanted excess hair growth (e.g., hirsutism) or alopecia, including alopecia areata, androgenic alopecia, anagen effluvium, telogen effluvium, or scarring alopecia. For example, a compound including a growth factor, such as a fibroblast growth factor, and/or a repair agent can be injected or otherwise delivered into one, two, or more hair root or follicles to modulate hair growth. For example, FGF, PDGF, KGF, IGF-1, and Substance P could potentially promote hair growth (and antagonists could potentially inhibit hair growth), PDGF, IL-1 alpha, FGF-5 and parathyroid hormone could potentially inhibit hair growth (while antagonists could potentially promote hair growth). 1, 25 dihydroxyvitamin D3 could potentially increase hair growth at low concentrations, and decrease hair growth at high concentrations.

Synergistically Enhancing Transdermal Penetration

In some embodiments, the treatment protocol includes the use of one, two, or more modalities to synergistically increase transdermal penetration of dermatologic preparations such as those disclosed herein. Not to be limited by theory, but some modalities increase permeability of dermatologic preparations through the stratum corneum layer. Such permeability-enhancing modalities could involve, but are not limited to one, two, or more of mechanical, chemical, thermal, and electromagnetic modalities, including sonophoresis and iontophoresis. In some embodiments, the permeability-enhancing modality involves applying a chemical peel to the skin, such as, for example, glycolic or salicylic acid, or a retinoid. While chemical solvents can be used with positive effect, in some embodiments they can undesirably dissolve, denature, or otherwise alter the dermatologic preparation. In some embodiments, the permeability-enhancing modality involves applying heat to the skin. In some embodiments, iontophoresis is employed. Iontophoresis (a.k.a. Electromotive Drug Administration (EMDA)) is a technique using a small electric charge to deliver a therapeutic agent transdermally by repulsive electromotive force using a small electrical charge applied to an iontophoretic chamber containing a similarly charged active agent and its vehicle. One or two chambers are filled with a solution containing an active ingredient and its solvent, also called the vehicle.

In some embodiments, the preparation can be administered under occlusion to synergistically increase penetration, in other words, to trap the preparation against the skin to increase penetration and effect. In some embodiments, an occlusive dressing includes a skin contacting barrier layer and an overlying backing layer. The backing layer can be stretchable and the barrier layer can include an elastic phase integrated by a cross-linked polymer network with water-absorbing hydrocolloid phase dispersed therein. The hydrocolloids could include, for example, carboxymethylcellulose (CMC), sodium CMC, karaya, gelatin and guar. A partially open cell foam may be used as the backing layer in order to provide some vapor transmission. The barrier layer and/or backing layer can include a film and/or an adhesive. The film could include a polyurethane, polyether ester, or polyetheramide material, or a combination thereof. In some embodiments, the backing layer could be moisture vapor permeable but water impermeable. In some embodiments, the preparation can be administered under occlusion for more than about, about, or no more than about 30 minutes, 1 hour, 2 hours, 4 hours, 6 hours, 8 hours, 12 hours, 24 hours, 48 hours, 72 hours, or more or less. In some embodiments, utilization of occlusion in combination with another modality such as ultrasound can decrease the occlusion time required to produce the desired clinical result. One embodiment of a method involving occlusion and sonophoresis is illustrated in the flow chart of FIG. 2.

In certain embodiments, the preparation can be configured to achieve a controlled occlusion of the skin, thereby resulting in optimal enhancement of biologically, active moiety penetration across the skin with minimal skin irritation. In certain embodiments, the composition may include a dispersing agent that aids in maintaining a particulate phase of the active ingredients dispersed in the continuous phase. In other embodiments, non-ionic excipients, such as lauric alcohol, propylene glycol monolaurate, myristyl lactate, lauryl lactate, or the like, facilitate dispersion.

In some embodiments, the preparation can function as a barrier to serve, for example, as additional skin protection as well as to increase penetration into the skin. The preparation could include, for example, a high lipid content and be based on water in oil emulsion, where the lipid content impedes the penetration of water into the skin. The skin could thus be sealed with a surface film. In some embodiments, the preparation includes one, two, or more components that correspond to or are substantially similar chemically and/or physically to the membranes of the natural stratum corneum. Substances such as ceramides, phytosterols, cholesterol, palmitic acid, and hydrogenated phospatidylcholine, for example, can cooperate in forming membranes and can stabilize the oil and water phases of creams. The lipid substances resulting from the secretion of sebum glands may also be added to barrier creams. Shea butter is a possible ingredient as it contains lipid substances as well as phytosterols. Besides its membrane forming functions, saturated (hydrogenated) phosphatidylcholine also supplies palmitic and stearic acid, both released from the molecule by enzymatic cleavage. Besides shea butter, there are other lipophilic substances like squalane which is a hydrogenated form of squalene, the preliminary stage of natural cholesterol, as well as physiological triglycerides of vegetable origin. In some embodiments, the composition includes amides like palmitamide MEA, stearamide MEA, urea and allantoin.

Sonophoresis, among other systems and methods disclosed herein, can synergistically increase the absorption of dermatologic preparations into the skin, and is defined herein as application of ultrasound to the skin resulting in enhanced transdermal transport of a desired dermatologic preparation. In some embodiments, transdermal absorption of the growth factor preparation, and/or the DNA repair enzyme containing preparation is synergistically increased by at least about 5%, 10%, 20%, 30%, 40%, 50%, 60%, 75%, 100%, or more, and/or has an enhanced clinical effect compared with application of the same amount of growth factor preparation, and/or the DNA repair enzyme containing preparation without the sonophoresis or other mechanism to increase transdermal transport. As discussed elsewhere in the application, the enhanced clinical effect could be, for example, reduction or elimination of fine lines and wrinkles, improvement in uneven skin tone and discoloration, decrease in undereye circles, swelling, and crow's feet, reversal of photodamage, reduction in size or number of acne, cysts, warts, eczema, actinic keratosis, seborrheic keratosis, and the like.

Not to be limited by theory, ultrasound waves can stimulate micro-vibrations within the skin epidermis and increase the overall kinetic energy of molecules making up topical agents. Ultrasound can increase drug transport by, for example, cavitation, microstreaming, and heating. Examples of sonophoresis systems and methods can be found, for example, in U.S. Pat. Nos. 4,767,402 and 6,190,315 to Kost et al., U.S. Pat. No. 6,030,374 to McDaniel, and Pahade et al., Intl. J. Pharm. Sci. Rev. and Res. Vol 3. issue 2, July-August 2010 pp. 24-32, all of which are hereby incorporated by reference in their entireties.

The ultrasound system includes one or more transducers operated at a frequency such as disclosed below for example, using appropriate electrical signal generators and amplifiers. Other ultrasound parameters including, but not limited to, amplitude, duty cycle, distance from the skin, and application time may be varied to achieve sufficient enhancement of transdermal transport.

The ultrasound system could include, in addition to the transducer, a portable (such as hand-field) or bench-top ultrasound generator. The ultrasound generator also may include circuitry for measurement of skin resistance. The transducer is placed against or near the skin and ultrasound is activated for a defined period of time. Subsequent application of chemical enhancers or physical driving forces can be applied using the same device or a separate device. Dermatologic preparations can be delivered from the device in some embodiments.

Ultrasound parameters may be determined in accordance with the desired clinical result, and particularly tailored to significantly increase transdermal absorption of the growth factor(s) and DNA repair enzyme(s) in some embodiments. In some embodiments, the ultrasound frequency utilized may be between about 1 kHz and about 31 MHz, such as between about 20 kHz and about 3 MHz, between about 20 kHz and 100 kHz, between about 0.5 MHz and about 1.5 MHz, between about 0.7 MHz and about 1.2 MHz, between about 0.9 MHz and about 1 MHz, about 1 MHz, or between about 3 MHz and 16 MHz if high-frequency ultrasound is utilized.

In some embodiments, the intensity utilized could be between about 0 and 20 $W/cm^2$, between about 0 and 10 $W/cm^2$, between about 0 and 5 $W/cm^2$, between about 0 and 3 $W/cm^2$, between about 0.2 and 2.0 $W/cm^2$, or between about 0.5 and 2 $W/cm^2$. In some embodiments, the intensity utilized could be no more than about 20 $W/cm^2$, 10 $W/cm^2$, 5 $W/cm^2$, 3 $W/cm^2$, 2.5 $W/cm^2$, 2 $W/cm^2$, 1.5 $W/cm^2$, 1 $W/cm^2$, 0.8 $W/cm^2$, 0.6 $W/cm^2$, 0.4 $W/cm^2$, or 0.2 $W/cm^2$. In some embodiments, the intensity utilized could be at least about 0.2 $W/cm^2$, 0.4 $W/cm^2$, 0.6 $W/cm^2$, 0.8 $W/cm^2$, 1 $W/cm^2$, 1.5 $W/cm^2$, 2 $W/cm^2$, 2.5 $W/cm^2$, 3 $W/cm^2$, 5 $W/cm^2$, 10 $W/cm^2$, or 20 $W/cm^2$ or more.

In some embodiments, the ultrasound or other synergistic modality treatment could be delivered in either a continuous or pulsed manner, or a combination of the two with a duty cycle of between 0-100%. For pulsed delivery, for example, the duty cycle could be no more than about 95%, 90%, 80%, 70%, 60%, 50%, 40%, 35%, 30%, 25%, 20%, 15%, 10%, or less, or between about 10-50%, or 20-30% in some embodiments.

In some embodiments, the on cycle could be between about 1.0 msec to about 1 sec, such as between about 2.0 msec to about 100 msec, between about 2.0 msec to about 50 msec, or between about 2.0 msec to about 20.0 msec.

In some embodiments, the transducer can be positioned on the skin, or at a distance from the skin between 0.1 and 10 mm, such as between about 0.1 and 5 mm, or 0.1 and 1mm in some embodiments. The ultrasound is preferably administered to the skin or at a site selected based on convenience to the patient as well as maximum penetration of the dermatologic preparation. For example, the arm, thigh, and stomach represent areas of relatively thin skin and high surface area, while the hands and feet are uneven and callused. In some embodiments, ultrasound is applied first to increase the permeability of the skin and then the dermatologic preparation is applied to the site where it diffuses through the skin or is otherwise transported through the skin.

The sonophoresis or other synergistic modality treatment time could vary depending on the clinical result, but could be in some cases between about 20 seconds and 30 minutes, such as between about 2 minutes and 15 minutes, between about 5 minutes and 10 minutes, or between about 5 minutes and 8 minutes. In some embodiments, the treatment time in minutes could be less than about 60, 45, 40, 30, 25, 20, 15, 12, 10, 9, 8, 7, 6, 5, 4, 3, 2, 1, 0.5, 0.3 minutes or less.

In some embodiments, the beam profile may be a collimated beam with precise control of output. In some embodiments, a focused beam may also be suitable. Some embodiments may provide a feedback warning if the operator loses contact with the skin, thus ensuring optimal treatment technique.

Permeabilizing ultrasound can be applied for a predetermined amount of time or can be applied only until permeabilization is attained. Since skin conditions can change over time, based on aging, diet, stress, and other factors, in some embodiments an operator could optionally measure permeability as ultrasound is applied to ensure sufficient ultrasound is applied and to minimize the risk of skin damage. Several methods can be used to determine when sufficient permeabilization has been reached. One way is to measure relative skin conductivity at the permeabilization site versus a reference point. These measurements are performed by applying a small AC or DC electric potential across two electrically isolated electrodes in contact with skin. The electric current flowing through these electrodes is measured using an ammeter and the skin resistance is measured using the values of the potential and the current.

Another way to determine when sufficient permeabilization has been reached is to measure absolute conductivity. Fully pertneabilized skin should have a resistance of no more than about 5 kohms in most situations. The degree of permeability can also be monitored using a sensor that determines the concentration of the dermatologic preparation being delivered. As the permeability decreases, the dermatologic preparation concentration could decrease.

The skin could be, in some embodiments, permeable for at least 30 minutes, at least an hour, or two hours. Under some conditions, the skin may remain permeable for up to eight to ten hours. It may be desirable to repermeabilize the skin with another dose of permeabilizing ultrasound under the same, or different conditions.

Several methods may be useful to attain or maintain permeabilization for an extended period of time. Cavitation enhancers, as described more fully below can be used. The chemical and physical enhancers and driving forces described below may also act to keep the skin permeable. In addition, large molecules such as sodium lauryl sulfate, for example, may permeate the skin and serve as spacer molecules to keep the skin open.

Further adjuncts to the process which increase permeability of skin or decrease skin barrier function may also be used. Options for this include, but are not limited to, stripping, removing, thinning or diminishing the structure, function, thickness or permeability of the stratum corneum by various mechanical, abrasive, photo acoustical, ablative, thermal, chemical, abrasive or enzymatic methods. Examples of these could include solvent or tape stripping, scrubbing, laser ablation or vaporization, chemical peeling, microdermabrasion, enzyme peeling, or laser treatment using high peak power, and/or short pulse duration lasers. One such embodiment may be an enzyme peel, which is formulated to specifically remove only the dead stratum corneum cells.

Transdermal transport enhancers that can be applied before, during or after the permeabilizing ultrasound include physical driving forces and chemical enhancers or driving forces.

Chemical enhancers include lipid bilayer disrupting agents and solubility enhancers. Chemical enhancers have been found to increase drug transport by different mechanisms. Chemicals that enhance permeability through lipids are known and commercially available. For example, ethanol has been found to increase the solubility of certain dermatologic preparations up to 10,000-fold and yield a 140-fold flux increase of estradiol through the skin, while unsaturated fatty acids have been shown to increase the fluidity of lipid bilayers. Examples of fatty acids that disrupt lipid bilayer include linoleic acid, capric acid, lauric acid, and neodecanoic acid, which can be in a solvent. Suitable solvents include water; dials, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones and other n-substituted-alkyl-azacycloalkyl-2-ones (atones).

Other chemical enhancers, not necessarily associated with binary systems, include dimethylsulfoxide (DMSO) or aqueous solutions of DMSO such as those described in U.S. Pat. No. 3,551,554 to Herschler; U.S. Pat. No. 3,711,602 to Herschler; and U.S. Pat. No. 3,711,606 to Herschler, and the azones (n-substituted-alkyl-azacycoalkyl-2-ones) such as noted in U.S. Pat. No. 4,557,943 to Coope.

Surfactants can act as solubility enhancers for some drugs as well as permeability enhancers by fluidizing the lipid bilayer. A preferred surfactant is sodium lauryl sulfate (SLS) present in an amount of about 0.25 to 5%, preferably about 1%. Other useful surfactants include fatty acids, fatty alcohols, esters of fatty acids, alkyl sulfonates, sodium salts of sulfonic acid or alkyl sulfonic acid, typically in a concentration in the range of 0.25 to 5% weight/volume.

Physical driving forces include suction, osmotic pressure gradient, concentration gradient, iontophoresis, electroporation, magnetic fields, additional ultrasound, and mechanical pressure.

Physical driving forces are preferably applied after the initial permeabilizing ultrasound to enhance transport of a dermatologic preparation into or through the skin or tissue. The driving force can be applied continuously over a period of time or at intervals during the period of permeabilization.

Mechanical pressure can be positive pressure or negative pressure, such as a vacuum. Suction may induce convective transport across the skin, thus enhancing the effect of ultrasound on transdermal transport.

Osmotic pressure gradients can be applied using salts (for example, 2 M NaCl) or sugars such as mannitol (1 M solution in saline) and dextrans.

Application of electric current enhances transdermal transport by different mechanisms. First, application of an electric field provides an additional driving force for the transport of charged molecules across the skin (electrophoresis) and second, ionic motion due to application of electric fields may induce convective flows across the skin, referred to as electrostnosis. This mechanism is believed to play a dominant role in transdermal transport of neutral molecules during iontophoresis. Iontophoresis involves the application of an electrical current, preferably DC, or AC, at a current density of greater than zero up to about 1 mA/cm$^2$. Typically, a constant voltage is applied since resistance changes over time, usually in the range of between greater than zero and four volts.

Application of magnetic fields to the skin pretreated with ultrasound may also result in a higher transport of magnetically active species across the skin. For example, polymer microspheres loaded with magnetic particles could be transported across the skin using sonophoresis and magnetic fields.

Application of pulsing electromagnetic fields (PEMF) of low energy or continuous electromagnetic fields could also synergistically be used in combination with the preparations and other modalities disclosed herein for a desired treatment effect. There are numerous parameters associated with a treatment apparatus that delivers PEMF. Such parameters include, but are not limited to, wave shape, frequency, pulse rate, burst rate, burst repetition rate, peak signal amplitude, induced electric field, duration, and others. These parameters may be altered or adjusted to achieve a particular configuration that will elicit the desired bioeffect on a molecule, cell, tissue, or organ.

PEMF parameters may be configured to promote interaction of ions with regulatory molecules, such as calcium binding to calmodulin. Use of this calcium-calmodulin pathway is based upon its known roles in acceleration of tissue repair, for example promotion of hair maintenance, growth, and restoration. Growth factors such as platelet derived growth factor (PDGF), fibroblast growth factor (FGF), and epidermal growth factor (EGF) are all involved in appropriate stages of hair maintenance, growth, and restoration. Moreover, angiogenesis and neovascularization are also integral for skin functionality including hair maintenance, growth, and restoration and may also be modulated. It is also thought that levels of prostaglandins (some which promote hair growth and some which inhibit hair growth) may be important in regulating hair growth and/or hair loss. The loss of hair may also be inflammatory in nature. All of these effects are dependent on the interaction of calcium with calmodulin. Thus, a waveform that utilizes a pathway that promotes the interaction of calcium with calmodulin can have physiologically significant bioeffect on hair maintenance, growth, and restoration. It is believed that in this way, PEMF encourages hair follicles to advance from a quiescent resting phase to a growth phase and/or limits or eliminates hair loss. In one embodiment, the apparatus that delivers PEMF is self-contained, lightweight, and portable. In some cases, the apparatus may also be disposable. The apparatus is preferably safe for home use, so that individuals may use the method on their own. In another embodiment, a miniature control circuit is coupled to a generating device, such as an electric coil via a connector. The miniature control circuit is designed to configure waveforms that produce physiologically beneficial results when applied to hair.

In some embodiments, the parameters of the frequency output are as follows: carrier frequency of between 1-50 MHz, such as 27.12 MHz±150 KHz; burst width and rate of 2 ms burst width at 2 Hz; peak power output of 0.5 Watt; average power (measured over 1 sec.) of 2 milli-watts; and a standard load of 50 Ohm.

A waveform configured using a specific embodiment may be applied to a target structure, such as a hair target pathway structure such as ions for a total exposure time of under 1 minute to 240 minutes daily. For example, the exposure time is about 15 minutes twice daily for 4-6 months. Alternatively, the exposure time may be about 15 minutes twice daily for an indefinite period of time. However, other exposure times may be employed.

Waveforms configured by the miniature control circuit are directed to a generating device such as electrical coils via a connector. The generating device delivers a pulsing magnetic field that can be used to provide treatment to the skin, including the scalp and/or hair. The miniature control circuit applies a pulsing magnetic field for a prescribed time and can automatically repeat the application of the pulsing magnetic field for as many applications as are needed in a given time period, for example 10 times a day. The miniature control circuit can be configured to be programmable, applying pulsing magnetic fields for any time repetition sequence.

A specific embodiment can be configured to treat a skin condition or hair by being incorporated into, or by otherwise including, a positioning device, thereby making the unit self-contained. Advantageously, miniature circuitry and ultra lightweight coils allow for convenient use of the apparatus. In this way, treatment of the skin, hair maintenance, growth, and restoration may be accomplished and enhanced anywhere and at anytime. Additionally, in certain embodiments, the apparatus is preferably placed around the desired treatment area such as the scalp or head region in order to treat patients with hair loss disorders affecting the scalp or head region. Preferably, the apparatus is adjustable, so that it may accommodate the different and varied sizes and shapes of scalps and heads. The apparatus may, for example, be incorporated into an article, such as a hat, so that the apparatus may be worn inconspicuously. The apparatus may further incorporate a disposable battery. Alternatively, the apparatus may incorporate a rechargeable battery.

Another embodiment applies a model to induce a time-varying electric field in a hair target pathway structure, such as ions and ligands (e.g., calcium-calmodulin), comprising about 0.1-100 msec bursts of about 1-100 microsecond rectangular pulses repeating at about 0.1-100 pulses per second. Peak amplitude of the induced electric field is between about 1 uV/cm and about 100 mV/cm, varied according to a modified function, inversely related to frequency. In another embodiment, the apparatus delivers PEMF in 2 ms bursts of 27.12 MHz sinusoidal waves repeating at 2 bursts/second, having a peak magnetic field of 0.05 G, which induces an average electric field of 32±6 mV/cm. In another embodiment, the apparatus delivers PEMF in 65 pec bursts of 27.12 MHz sinusoidal waves, inducing a 1 G high amplitude peak magnetic field, repeating at 600 bursts per second. In another embodiment, the apparatus delivers PEMF in 1 msec bursts of 27.12 MI-Iz waves at 5 bursts/second, with 0.02 G of peak amplitude. In a related embodiment, the apparatus delivers PEMF in 1 msec bursts of 27.12 MHz waves at 5 bursts/second, with 0.05 G of peak amplitude. In yet another embodiment, the apparatus delivers PEMF in 2 msec bursts of 27.12 MHz repeating at 5 bursts/second with a peak amplitude of 0.05 G. In one embodiment, the apparatus delivers PEMF in 2-20 msec bursts of 27.12 MHz waves having a peak amplitude of 0.1 G. In a related embodiment, the apparatus delivers PEMF in 2-20 msec bursts of 27.12 MHz waves having peak amplitude of 2.0 G. In yet another embodiment, the apparatus delivers PEMF in 2 msec bursts of 27.13 MHz waves repeating at 5 bursts/second with a peak power of 0.05 Gauss. Further parameters of PEMF can be as described, for example, in U.S. Pat. Pub. No. 2013/0035539 A1 to Kornstein, which is hereby incorporated by reference in its entirety.

Additional ultrasound can be applied at higher, lower, or the same frequency as the initial permeabilizing ultrasound. In other cases, it may be preferable to use lower frequency, "maintenance" doses of ultrasound to keep the skin permeabilized.

Greater transdermal transport can be achieved by inducing cavitation either inside or outside of the skin. Cavitation is the growth and oscillations of air bubbles present in fluids and air pockets present in the keratinocytes of the stratum corneum. Application of low-frequency ultrasound appears to induce cavitation inside as well as outside the skin and disorganize the stratum corneum lipid bilayers thereby enhancing transdermal transport. In addition, oscillations of cavitation bubbles may result in significant water penetration into the disordered lipid regions and may cause the formation of aqueous channels through the intercellular lipids of the stratum corneum. This allows transport of permeants across the disordered lipid domains, then across keratinocytes and the entire stratum corneum. This transport pathway may result in an enhanced transdermal transport as compared to passive transport because the diffusion coefficients of permeants through water, which is likely to primarily occupy the channels generated by ultrasound, are up to 1000-fold higher than those through the ordered lipid bilayers, and the transport path length of these aqueous channels may be much shorter (by a factor of up to 25) than that through the tortuous intercellular lipids in the case of passive transport.

Cavitation can be enhanced by providing nuclei in the form of gas bubbles, crevices, or particulate. Examples of cavitation enhancers include fluorocarbons, particulate matter (for example, microspheres, silica, titanium dioxide particles, polymer particles), gases (for example, argon, air), and stabilized air bubbles.

Occurrence of cavitation on the skin surface may also be enhanced by coating the skin surface with a wetting agent in the entire area of application of ultrasound except for a spot. Cavitation may preferentially occur at the spot due to the difference in wetting properties of the skin and the coating. The coating may be made from a polymer such as poly (methyl methacrylate) or it may be a membrane made from poly(vinyl difluoride), for example.

Transdermal transport enhancement induced by ultrasound increases with increasing ultrasound pressure amplitude. However, application of high ultrasound pressure amplitudes is prohibited by the discomfort associated with it. The extent of discomfort induced by ultrasound increases with increasing application area, probably due to exposure of more pain receptors to ultrasound. Application of high energy ultrasound to a small area may avoid excessive pain and provide optimal conditions for dermatologic preparation delivery. It is possible to achieve application of ultrasound to a small area using geometric channeling or using a vibrating element as described in WO 98/00194 by Sontra. Alternatively, in some cases, it may be preferable to apply the dermatologic agent to a larger skin surface area, in which case diffuse ultrasound would be preferred.

In some embodiments, the ultrasound can be applied through a cavity filled with an aqueous or non-aqueous coupling medium. The coupling medium increases the efficient transfer of ultrasound energy from transducer to the skin. Appropriate mixtures of these coupling media may also enhance cavitation activity near the skin or inside the skin, increasing permeability and effectiveness of transport of molecules into or across the skin. The coupling medium can also serve as the medium for delivery of the dermatologic preparation, or may be removed before delivery of the dermatologic preparation.

The coupling medium can include, but is not limited to, water, saline, alcohols including ethanol and isopropanol (in a concentration range of 10 to 100% in aqueous solution), surfactants such as Triton X-100, SLS, or SDS (preferably in a concentration range of between 0.001 and 10% in aqueous solution), DMSO (preferably in a concentration range of between 10 and 100% in aqueous solution), fatty acids such as linoleic acid (preferably in a concentration range of between 0.1 and 2% in ethanol-water (50:50) mixture), azone (preferably in a concentration range of between 0.1 and 10% in ethanol-water (50:50) mixture), polyethylene glycol in a concentration range of preferably between 0.1 and 50% in aqueous solution, histamine in a concentration range of preferably between 0.1 and 100 mg/ml in aqueous solution, EDTA in a concentration range of preferably between one and 100 mM, sodium hydroxide in a concentration range of preferably between one and 100 mM, and combinations thereof.

In the case of delivery of the dermatologic preparation, the coupling medium also can contain an agent that is transported across the skin by diffusion or other driving forces including convection and iontophoresis.

The coupling medium can also optionally include a chemical enhancer. Transport enhancement may be obtained by adding capillary permeability enhancers, for example, histamine, to the coupling medium. The concentration of histamine in the coupling medium may be in the range, for example, of between 0.1 and 100 mg/ml. These agents may be delivered across the epidermis during application of ultrasound and may cause local edema that increases local fluid pressure and may enhance transport across the skin. In addition, the occurrence of free fluid due to edema may induce cavitation locally so as to enhance transport across the skin.

In some embodiments, one, two, or more other energy-based therapeutic modalities can be utilized to promote synergistic transdermal enhancement, including but not limited to: a radio-frequency (RF) source, e.g., an RF source coupled to an RF electrode, a coherent source of light, e.g., coupled to an optical fiber, an incoherent light source, e.g., coupled to an optical fiber, a heated fluid, e.g., coupled to a catheter with a closed channel configured to receive the heated fluid, a heated fluid coupled to a catheter with an open channel configured to receive the heated fluid, a cooling source, e.g., a cooled fluid coupled to a catheter with a closed channel configured to receive the cooled fluid, a cooled fluid coupled to a catheter with an open channel configured to receive the cooled fluid, a cryogenic fluid, a resistive heating source, a microwave source coupled to a microwave antenna, and/or a fluid jet. Energy sources can include, without limitation, one or more transducers, such as acoustic transducers, ultrasound transducers, magnetic transducers, electro-magnetic transducers, pressure transducers (e.g., mechanical impulse transducers), and other types of transducers suitable for use on a subject. The transducers can be energized to output penetrating energy that causes cell stimulation or activation. The non-light energy delivery system, in some embodiments, may be a field generator (e.g., an electro-magnetic field generator), radiofrequency emitter, vibrator (e.g., an unbalanced mass vibration system), electrical stimulator (e.g., electrical stimulators configured selectively output low levels to high levels of electrical currents), magnetic stimulator, and the like.

In some embodiments, delivery of skin compositions including one or more growth factors and DNA repair enzymes as disclosed herein can be performed using a non-invasive radio frequency (RF)-controlled device, such as, for example, described in U.S. Pat. No. 8,467,868 to Mohapatra et al., which is hereby incorporated by reference in its entirety. The RF device can be placed over a formulation dispenser. The formulation dispenser can includes a container connector attached to the flexible container and an applicator having a sealed piercing member with the container connector. An porous applicator membrane has enlarged holes for passage of a composition, for example, in gel or liquid formulation. The gel formulation dispenser pierces a seal in the container and delivers the gellliquid formulation from the container to the application site with the RF device. Flow rate of the drug or other small molecule gel formulation is controlled by the optimized RF frequency. Local inflammation and inability to deliver various skin compositions are some of the major problems with current transdermal drug delivery systems. RF devices can be used in using ablative or non-ablative methods to rejuvenate the skin. Radiofrequency (RF) devices have been used to induce tightening of the skin via a uniform volumetric heating into the deep dermis. The technique was found to produce gradual tightening in most cases. Delivery of skin compositions transdermally may be improved by temporarily increasing the skin pore sizes with controlled application of heat. A non-ablative RF device can also synergistically improve skin conditions including laxity, wrinkles, clarity, and pore size. In some embodiments, RF electrodes may be maintained either in contact with the skin, or in vicinity of the skin, up to, for example, a distance of about 500 microns therefrom. In some embodiments, an electrical current can be applied having a frequency between about 10 kHz and 4000 kHz, such as between about 10 kHz and 500 kHz, or about 100 kHz. The device 500 could include a pulse generator 540, at least one monopolar or bipolar electrode array 510 comprising one, two, three, four, five, six, or more electrodes connected by electrode lead(s) to the skin, or wirelessly. The leads 510 can be powered by a power source 540, such as a battery. The power source in some embodiments could transmit energy to an energy (e.g., RF) receiving power circuit via inductive coupling. The parameters of the device and the stimulating current (voltage, frequency, pulse width, etc.) can be adjusted according to the desired clinical result. In some embodiments, the frequency may be between about 100 Hz and 500 Hz, such as between about 150 Hz and 250 Hz, or between about 160 Hz and 200 Hz. The pulse width could be, in some embodiments, between about 30 microseconds and about 240 microseconds, such as between about 60 microseconds and about 180 microseconds, or less than about 180, 150, 120, 90, 60, 45, 30, or less microseconds. The amplitude of stimulation could be less than about 5, 4.5, 4, 3.5, 3, 2.5, 2, 1.5, 1, 0.5, or less volts in some embodiments. The RF energy component could include features present, for example, in U.S. Pat. Pub. No. 2006/0184209 to John et al., which is hereby incorporated by reference in its entirety. In some embodiments, an RF-based system can include lead wires may lead from the circuitry and be coupled to electrodes 1230 disposed on targeted areas of the skin. The circuitry may be operable to harvest and store RF energy, control the operation of the device and provide pulses and signals to the targeted areas of the skin. The RF component could have a discrete controller or communicate, such as wirelessly, with an external controller. For a system with a microwave rather than an RF energy component, one or more microwave antennas would be present rather than the electrodes, and a microwave generator would be present rather than an RF power source. In some embodiments, the microwave energy source may be configured to deliver less than about 600, 500, 400, 300, 200, 100, 90, 80, 70, 60, 50, 40, 30, 20, 10, 5, 3, 2, 1, or less joules/cm2 to the target tissue in a treatment session. Further RF-based systems that can be used with systems and methods described herein include the THERMAL E system by Solta Medical (Hayward, Calif.), described, for example, in U.S. Pat. Nos. 5,660,836, 6,749,624, 7,189,230, and 8,221,410 to Knowlton, each of which are hereby incorporated by reference in their entireties.

In some embodiments, a skin care brush, used prior to and/or following application, can synergistically increase the absorption of dermatologic preparations into the skin. Power skin care brushes, such as those useful for cleansing of the facial region, are typically driven directly, such as by a drive shaft or shafts, gears and a motor. The skin brush can include one, two, or more brushheads, with a plurality of bristle/filament tufts, which move in unison. Some brushheads rotate)(360° in one direction continuously, while others oscillate through a selected angle. The higher frequency skin brushes are often referred to as sonic or sonic frequency brushes. The frequency range of such brushes can be, e.g., 120-300 or 120-600 Hz, usually producing some slight bristle tip flexing or whipping in addition to oscillation of the bristles. Such separate bristle tip movement usually does not occur in the lower speed scrub-type brushes. An example of such a sonic skin brush appliance and a brushhead is described in U.S. Pat. No. 6,032,313 to Tsang, U.S. Pat. No. 7,320,691 to Giulani et al., and U.S. Pub. No. 2012/0233798 A1 to Brewer et al., the contents of which are hereby incorporated by reference in their entireties.

In sonic cases, the brushhead and drive system are configured so that portions of the bristle field of the brushhead move in different directions or move out-of-phase with the other portions. Such a particular movement may have advantages in facial cleaning, including the possibility of producing better cleansing with less discomfort. The brushhead assembly can include several concentric brush field portions, which are independently driven by separate mechanical means. In some embodiments, a brushhead arrangement provide out-of-phase and/or counter-rotation action between different groups of bristle tufts but is driven by a single drive mechanism.

Facial Skin Treatment Protocol

Figure 5:
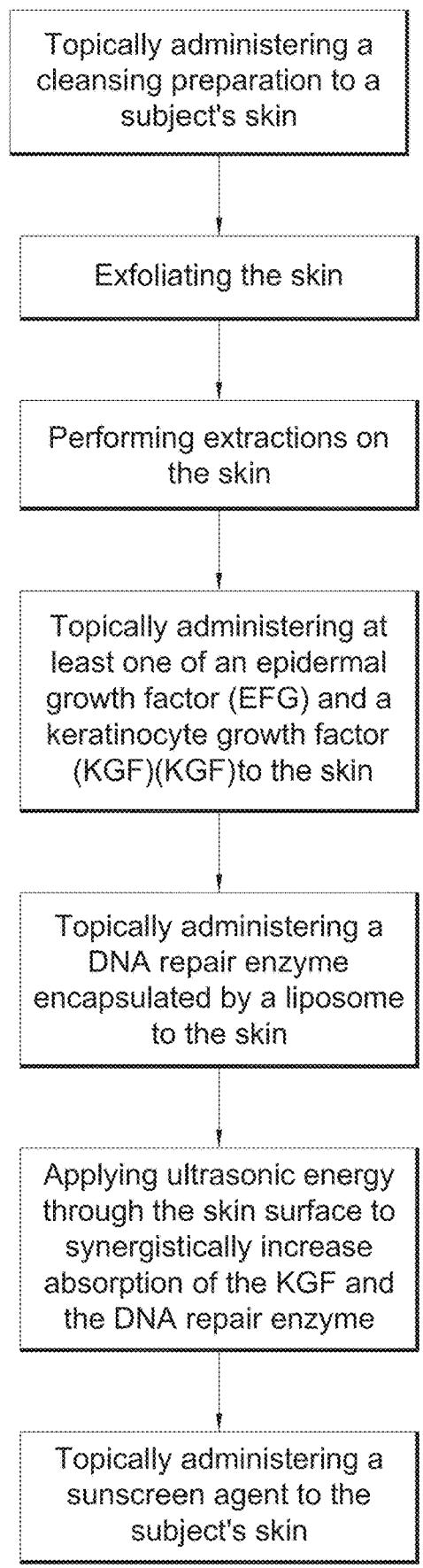
FIGS. 5-6 are flow charts illustrating a skin care method involving a modality to synergistically increase transdermal penetration of one or more dermatologic preparations, according to some embodiments of the invention.
Figure 6:
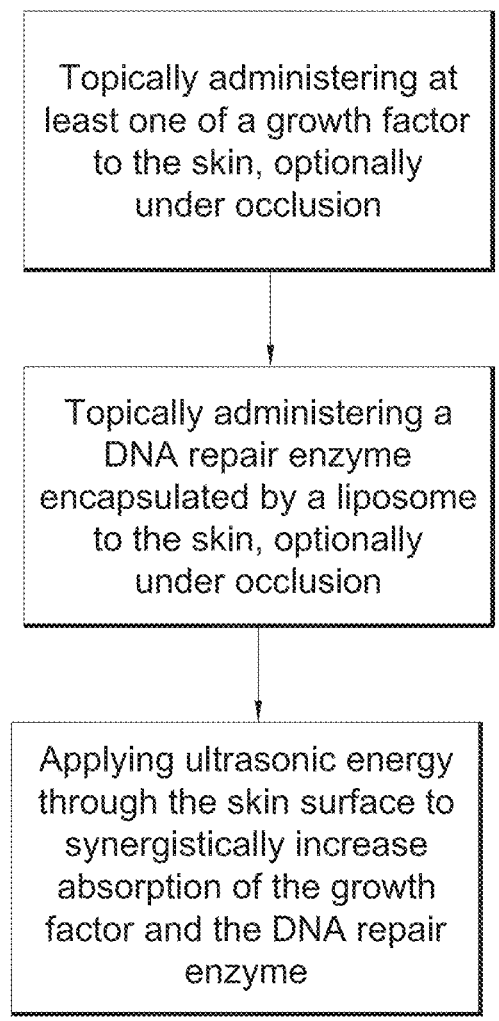

A facial skin treatment protocol will be described, and a flow chart illustrated in FIG. 5. As discussed elsewhere, the steps need not be performed in the particular order listed, and steps could be repeated or omitted as well. While described primarily in context of the face, the protocol could be modified to include any desired area of a patient's skin.

A cleanser, such as a renewal Foaming Cleanser preparation is applied to the skin. The preparation can then be removed with a warm facial cloth. Waterproof mascara can be removed using an eye makeup remover (e.g., for between about 1-6 minutes, such as about 4 minutes).

Skin analysis and diagnosis, under the naked eye and/or a magnifying lamp, can be performed, and discussed with the patient (e.g., for between about 1-5 minutes, such as about 2 minutes).

Exfoliation can be performed using an exfoliant, such as an alpha or beta-hydroxy acid peel or salicylic acid peel, for example, which can be placed onto a cotton pad and when wet, then applied carefully to the affected skin, such as the face or neck region. The exfoliant is left on the skin for about 4-8 minutes, such as about 6 minutes, unless the skin becomes uncomfortable. The patient can be cooled using a fan, and/or scalp massage performed while the exfoliant is on the skin. The exfoliant can then be removed with a warm facial cloth, and the skin rinsed with cool water. In some embodiments, this step can be performed between about 7-15 minutes, such as about 11 minutes. In some embodiments, exfoliation of the patient's hands and/or feet can be done simultaneously, or in a separate step, such as for about 1-5 minutes, such as about 2 minutes.

The exfoliant can then be removed from the patient's hands and/or feet with a warm wash cloth, and then dried. A EGF and/or KGF-containing growth factor preparation can then be applied, and allowed to thy thoroughly. An Intensive Renewal preparation can then be applied. In some embodiments, this step can be performed for about 1-5 minutes, such as about 2 minutes.

Extractions, e.g., for acne, can then be performed manually utilizing an appropriate extraction tool, such as for between about 2-10 minutes, such as about 5 minutes or about 7 minutes.

An eye renewal preparation can then be applied to the periorbital and eyelid area, and a night renewal preparation can then be applied and massaged into the face, neck, hands, feet, and/or décolleté area and left on the skin. Steam or mist can optionally be utilized with this step. This step could take between about 3-20 minutes, such as about 5 minutes or about 10 minutes in some embodiments.

A mask, such as a Ginseng Herbal Mask can then be applied to the face, and additional eye renewal preparation to the periorbital and eyelid area. In some embodiments, masks suitable for use with systems and methods disclosed herein include one or more piece, disposable or reusable facial masks. Some masks can be made of cloth or synthetic materials and have cut-outs or slits for the eyes, nose, and mouth. In other embodiments, facial masks are applied directly to the skin in a clay, peel-off, or mud form. Such masks can purge the skin of impurities as the mask hardens, and then it is rinsed off. Many of them contain chamomile, lavender, eucalyptus, and fruits, which contain essential oils known to have healing properties when inhaled. Masks can fit a standard-size face, or be customizable to a particular patient. In some embodiments, the masks are pre-infused with a hydrating fluid, e.g., a water-based agents or extracts of green tea, aloe, or red ginseng. The mask contents can have beneficial ingredients including vitamins. A mask can be heated, cooled, or both in order to increase the efficacy, absorption, or other effect on the patient's skin.

Masks can enhance the complexion using, for example, clay, mud, cucumber, and avocado. These masks are designed to cleanse the pores of the face to remove impurities and excess oils which clog the pores and can cause blemishes. Some of these masks also firm and refresh the face leaving the complexion looking less stressed. They are applied to the face using fingers and usually originate from a disposable tube or container. The masks are then allowed to dry for a time ranging from 5 minutes to 15 minutes (an approximation) and are either rinsed off or peeled off depending on the type of mask used. In some embodiments, a reusable mask can be constructed of nonporous rubber or similar material to apply medications to the face, such as described in U.S. Pat. No. 3,211,146 to Rodelli, hereby incorporated by reference in its entirety. Other types of reusable masks consist of holes cut out to allow the eyes to see and avoid contact with any medications, such as described in U.S. Pat. No. 3,354,884, hereby incorporated by reference in its entirety. This type of mask is designed primarily to apply pressure to the face to reduce any puffiness or swelling and moisturize utilizing a saturated pad attached to the inside of the mask. Some reusable masks employ electrical-stimulating elements located on the inside of the mask and pressed around key areas, such as the eyes, having an acupuncture-type effect to alleviate headaches or sore muscles. Still, others have focused primarily on moisturizing the face by utilizing straps or fasteners to press lotions or creams onto the face and neck for various lengths of time. Other masks can be as disclosed in U.S. Pat. Pub. No. 2007/0023048 to Cho, such as a one-use, disposable mask constructed of a plurality of layers of highly porous surface material enclosing an interior filled with an effusable substance, such as black tea, green tea, herbal tea, herbal essence, chamomile, lavender, eucalyptus, or fruits. The layers of the porous material are attached to each other at the boundary of the mask and in striping across the mask, forming small sections over the entire mask so that the effusable substance within remains evenly distributed across the face. A nose slit is provided for breathing while the mask is laid on the face.

While the mask in on, the patient's hands, arms, neck, and shoulders can be massaged. The mask can then be removed with a warm facial cloth. This step could take between about 3-15 minutes, such as about 5 minutes or about 10 minutes in some embodiments.

A growth factor, e.g., an EGF and/or KGF-containing preparation can then be applied to the skin, such as the face and neck, and allowed to dry thoroughly for about 2-15 minutes, such as about 5 minutes or about 10 minutes in some embodiments.

Sonophoresis, such as described above, can then be performed to synergistically increase absorption of the dermatological preparation(s), such as the EGF and/or KGF preparation, and/or the DNA repair enzyme containing preparation depending on the desired clinical result. In one non-limiting embodiment, pulsed ultrasound having a frequency of between about 0.7 MHz and 1.1 MHz, an on-time of between about 2.0 msec to about 20.0 msec, a duty cycle of between about 20-30%, and an intensity of between about 0 and 3 W/cm$^2$ is delivered for approximately 1 to 15 minutes, such as about 3 minutes, 5 minutes, or 10 minutes.

An Intensive Renewal preparation can then be applied to the face, neck, and/or décolleté area for approximately 1 to 10 minutes, such as about 3 minutes or about 5 minutes.

A sunscreen preparation, such as at least about SPF 30, 45, 60, or more, can then be applied to the face and neck for approximately 1 to 7 minutes, such as about 3-4 minutes.

DNA Repair Enzyme Formulations

The technology includes formulations, systems, and methods that include one, two, or more DNA repair enzymes. The DNA repair enzymes can be encapsulated, either separately or in combination, by liposomes. The compositions and methods can employ a carrier suitable for administration to a subject, such as in an oral, rectal, intravenous, intramuscular, subcutaneous, transdermal, or other formulation for example.

In one embodiment, the DNA repair enzyme is encapsulated by liposomes. In various embodiments, a composition can further include one or more pharmaceutically acceptable excipients. In some embodiments, a composition can further include one or more additional DNA repair enzymes. In certain embodiments, a composition can further include one or more additional therapeutic and/or components (e.g., cosmetic, fragrance, coloring, emollient, preservative, and the like). In various embodiments, a composition can be used for DNA protection and/or repair. DNA can include nuclear and mitochondrial DNA. DNA can be DNA in a skin cell. Protection and/or repair can relate to damage resulting from electromagnetic radiation (e.g., ultra-violet (UV) and X-ray), oxidating and other toxins (e.g., environmental, dietary, pollution, medical such as chemotherapeutics), viral (e.g., herpes virus activation), oncogenic, autoimmune, burns, trauma, diabetic and decubitus ulcers, and the like.

With regard to method of administration, carriers and liposomes used to administer a DNA repair enzyme can be of various types and can have various compositions. However, carriers and liposomes generally should not be substantially toxic and a liposome generally should be able to deliver at least a portion of its contents into the interior of a cell.

Liposomes can be of various sizes and can have one or more membrane layers separating its internal and external compartments. A liposome can include a sufficient amount of enzyme to be sequestered so that only one or more liposomes are necessary to enter a cell for delivery of the DNA repair enzyme and/or growth factor. A liposome can be resistant to structural disruption. Liposome structures include small unilamellar vesicles (SUVs, less than 250 angstroms in diameter), large unilamellar vesicles (LUVs, greater than 500 angstroms in diameter), and multilamellar vesicles (MLs). SUVs can be used to administer DNA repair enzymes. SUVs can be isolated from other liposomes. Enzyme in a liposome can be incorporated by molecular sieve chromatography, which can be precise but time consuming and dilutes the liposomes, or differential centrifugation, which can be rapid but produces a wider range of liposome size.

A liposome can include natural and/or synthetic phospholipids, glycolipids, and other lipids and lipid congeners (e.g., cholesterol, cholesterol derivatives, and cholesterol congeners), charged species (e.g., which impart a net charge to the membrane), reactive species (e.g., which can react after liposome formation to link additional molecules to the liposome membrane), and other lipid soluble compounds (e.g., compounds having chemical or biological activity).

A liposome membrane can undergo a phase transition from crystalline to liquid at a temperature ($T_c$ characteristic of the phospholipid composition. When the phospholipid is heated above $T_c$ and then cooled, the membrane can retain water in its amphiphilic lattice and can have one or more characteristics of a gel. To achieve a liquid or gel state, the phospholipid composition should be such that the $T_c$ is lower than the temperature which inactivates the entrapped enzyme and/or factor. Cholesterol in the phospholipid mix can effectively reduce a $T_c$ by broadening a temperature range at which phase transition occurs. One suitable mixture for preparing a liposome includes phosphotidyl choline (or a derivative thereof with a $T_c$ of less than 42° C.), diacetyl phosphate (or a negatively charged species at neutrality), and cholesterol (or a cholesterol derivative). For example, the phosphotidyl choline, diacetyl phosphate, and cholesterol can be at a molar ratio of about 7:2:1.

In some embodiments, pH sensitive liposomes can be used with the technology. Liposomes can enter a cellular cytoplasm by endocytosis into a lysozyme having a low pH. Accordingly, liposomes which are stable at neutral pH but release their contents at acidic pH can be used to deliver enzymes into the lysozymes of the cytoplasm, whereupon the contents are released. Since various DNA repair enzymes (e.g., T4 endonuclease V) are relatively stable at low pH, such methods can facilitate delivery of an enzyme into a cell.

Liposomes can be made sensitive to the low pH of the lysozymes by the lipid composition. For example, a pH sensitive liposome can be prepared by using phospholipids that form lipid bilayers when charged but fail to stack in an ordered fashion when neutralized. One such a phospholipid is phosphatidylethanol amine, which is negatively charged above about pH 9. The net charge of a phospholipid can be maintained at a pH which would otherwise neutralize the head groups by including charged molecules in the lipid bilayer which themselves can become neutralized. Such charged molecules include oleic acid, cholesteryl hemisuccinate, and the like, which are negatively charged at about neutral pH but become neutralized at about pH 5. In some embodiments, neutral molecules, such as phosphatidylcholine, can also be added to a liposome where they do not interfere with stabilization of a pH sensitive phospholipid by a charged molecule.

Liposomes including phosphatidylcholine and phosphatidylethanolamine can be more pH sensitive than those of phosphatidylethanolamine alone. In some embodiments, liposomes having a molar ratio of cholesteryl hemisuccinate (CHEMS) to the remaining components of about 1:1 can to respond to pH changes faster than liposomes containing lesser amounts of CHEMS (e.g., minutes versus hours). Accordingly, in some embodiments, a composition for the pH sensitive liposomes can be phosphatidylethanolamine (PE), phosphatidylcholine (PC), oleic acid (OA), and CLIENTS in a molar ratio of about 2:2:1:5. Various compositions for producing pH sensitive liposomes can be used.

Liposomes can be prepared by combining a phospholipid component with an aqueous component containing the DNA repair enzyme under conditions resulting in vesicle formation. A phospholipid concentration generally should be sufficient to form a lamellar structure. An aqueous component generally should be compatible with biological stability of an enzyme. Methods for combining the phospholipid and aqueous components to form vesicles include: drying a phospholipids onto glass and then dispersing them in an aqueous component; injecting phospholipids dissolved in a vaporizing or non-vaporizing organic solvent into a heated aqueous component; and dissolving phospholipids in an aqueous phase with a detergent and then removing the detergent by dialysis. A concentration of a DNA repair enzyme in an aqueous component can be increased by lyophilizing the enzyme onto a dried phospholipid and then rehydrating the mixture with a reduced volume of aqueous buffer. SUVs can be produced from the foregoing mixtures by methods including sonication and dispersing the mixture ough small bore tubing or through a small orifice of a French press.

SUVs can be prepared by drying phospholipids onto glass, rehydrating them in aqueous buffer containing a DNA repair enzyme with shaking at 37° C., sonicating the resulting mixture, and isolating the SUVs containing the DNA repair enzyme by molecular sieve chromatography and concentrating the SUVs by centrifugation.

DNA repair enzymes incorporated into a carrier and/or liposomes can be administered to living cells through any desired route, e.g., internally and/or topically. For internal administration to animals or humans, it is preferable that the liposomes are relatively or substantially pyrogen-free and/or sterile. To eliminate pyrogens, pyrogen-free raw materials, including all chemicals, enzymes, factors, and water, can be used to form the liposomes. Sterilization can be performed by filtration of the liposomes through 0.2 micron filters or by any method known in the art. For injection, the liposomes are suspended in a sterile, pyrogen-free buffer at a physiologically effective concentration. For topical administration, it is preferable that a liposome preparation be relatively or substantially pyrogen-free and/or sterile. Liposomes can be suspended in a carrier material (e.g., buffered polymeric glycol gel) for application to the skin. In some embodiments, a carrier material does not include a non-ionic detergent, which can disrupt a liposome membrane. The concentration of the enzyme and/or factor in the final preparation can vary over a wide range, a typical concentration being on the order of about, at least about, or no more than about 100, 50, 25, 10, 5, 1 or 0.1 µg/ml. In the case of pH sensitive liposomes, lower concentrations of the DNA repair enzyme can be used, for example, on the order of about 0.001 to 10 µg/ml or about 0.01 to 1.0 µg/ml for liposomes administered to cells internally. Other concentrations can be used if desired.

One method for producing topically applied carriers and/or liposomes encapsulating biologically active proteins is exemplified by the procedure for encapsulation and administration of DNA repair enzyme. The biologically active protein can be electrophoretically pure. The biologically active protein can be encapsulated under conditions that do not inactivate the protein's biological activity. The concentration of liposomes necessary for topical administration can be determined by measuring a biological effect of the protein in liposomes on target skin cells in culture. Once an active range is found, equal or greater concentrations can be formulated in a composition such as a lotion or gel for application to skin, or oral or other formulations as described herein. One example of a dosage range of the final composition for application is in the range from about 20 to about 100 µl/cm².

The technology can include the use of a wide range of DNA repair enzymes. A DNA repair enzyme can be from essentially any organism, animal, plant, bacteria, or virus and can be in a pure, extract, or crude form. However, a DNA repair enzyme can be selected to have biological activity despite its origin and/or form.

Bacterial repair systems have been demonstrated to differ significantly from repair in human cells. However, bacterial enzymes such as enzyme endonuclease V (also referred to herein as T4 endonuclease V and den V endonuclease V) have the ability to enhance DNA repair in human cells. Enhanced DNA repair can be evidenced by one or more of increased UV-specific incision of cellular DNA, increased DNA repair replication, and increased UV survival after treatment with the enzyme.

The endonuclease V enzyme can be produced by the deny gene of the bacteriophage T4. T4 endonuclease V can catalyze a rate limiting, first step in the removal of UV-induced DNA damage, namely, single strand incision of DNA at the site of damage. In particular, T4 endonuclease V can exhibit glycosylase and apurinic/apyrimidinic endonuclease activities and can act at the site of ultraviolet induced pyrimidine dimers.

Other enzymes having the ability to repair DNA damage include O6-methylguanine-DNA methyltransferases, photolyases, uracil- and hypoxanthine-DNA glycosylases, apyritnidiniclapurinic endonucleases, DNA exonucleases, damaged-bases glycosylases (e.g., 3-methyladenine-DNA glycosylase), correndonucleases alone or in complexes (e.g., *E. coli* uvrA/uvrB/uvrC endonuclease complex), and other enzymes and enzyme such as, the products of the ERCC genes of humans and the RAD genes of yeast. Generally, a DNA repair enzymes can be enzymes having an ability to participate in repair of any damaged nucleic acid. Some DNA repair enzymes that can be used include hSMUG1, hMBD4, mismatch-specific thymine/uracil glycosylase, methylpurine DNA glycosylase, hNTH1 (human endonuclease III ehomolog), adenine-specific mismatch DNA glycosylase (human mutY homolog), 8-oxoguanine DNA glycosylase, 8-oxo-GTPase/8-oxodGTPase (Human MutT homolog), dUTPase, AP endonuclease, Mouse Aag, human DNA polymerase beta, *E. coli* Endonuclease III, *E. coli* Endonuclease IV, Human FEN-1, *E. coli* Fpg, *E. coli* mug, *E. coli* MutY DNA glycosylase, *M. thermoautotrophicum* TDG, *E. coli* uracil DNA N-glcosylase, and deoxyribose phosphate lyase.

*Micrococcus luteus* is one source for a UV-specific DNA endonuclease that has been used for at least topical application. This DNA repair enzyme has been determined to have the ability to reverse the amount of CPUs in the damaged DNA by localizing in the epidermis and targeting the backbone of the DNA near the dimer. *M. luteus* is a UV-resistant microbe found in marine waters and soil. It has been shown that *M. luteus* removes damaged DNA by stimulating the skin's natural process of DNA damage repair. When the *M. luteus* extract with endonuclease activity is encapsulated in a liposome, it will target the backbone of the DNA near the dimer. It excises the whole portion and synthesizes a new strand in the 5'-3' direction, inserting correct base pairs with their formerly damaged counterparts. The rejoining of the strands is facilitated by polynucleotide ligase. UV-endonuclease speeds natural recovery from sun damage by quickly recognizing sustained damage and targeting those cells. This repair enzyme will enhance correction of UV damage in the skin, as well as prevent future weakening of genetic material, which can cause photoaging and skin cancers. In vitro studies have demonstrated the ability of this enzyme to successfully enhance DNA repair following UV-induced damage, showing that cells treated with this DNA repair enzyme were more likely to survive after being exposed to UV radiation.

The liposome encapsulated *M. luteus* extract (with endonuclease activity) can decrease sensitivity to UV radiation on a reconstituted epidermis with increased sensitivity to UV damage by decreasing the stress on the cells. TNF-α as well as the interleukin isomers released in the cascade following UV exposure will contribute to immune system suppression, but lab tests have shown that their expression can be reduced with the addition of *M. luteus* extract with endonuclease activity. This cytokine cascade causes extraneous protease activity, which will cause the cells to become apoptotic and weakens the structure of the skin. Studies have found a −0.6% decrease in the ability of DNA repair capacity per year as patients aged.

Another example is the OGG-1 repair enzyme, which uses base excision repair to excise 8-oxo-G and repair damage from reactive oxygen species. In base excision repair (BER), one specific base is removed by a glycosylase enzyme, and is replaced with the correct base by DNA polymerase. An encapsulated form of 8-oxo-guanine glycosylase (OGG1) can be used to reverse the damage caused by free radicals. One in vitro study has shown complete removal of 8-oxo-G by OGG1 and therefore repairs of oxidative DNA damage. Furthermore, liposomal delivery of OGG1 into human keratinocytes dramatically increases the rate of 8-oxo-G repair. Topical, among other routes of administration of OGG1 can potentially result in decreased tumor size and dramatically reduced tumor progression.

OGG1 can be utilized with a delivery system utilizing pH changes. Once this enzyme is encapsulated in a liposome and applied, it can penetrate into the desired tissue layer, e.g., the epidermis or an endothelial cell layer. If the phospholipid encounters a region of changed pH, the liposome will burst and release the enzyme into the cell. Through this method, liposomes are able to penetrate deep into the dermis or other deeper cell layers, where they can be absorbed and utilized to repair damaged DNA.

Photolyases are another example of DNA repair enzymes. A distinctive source for these enzymes is from the cyanobacteria group Anacytsis nidulans. These proteins contain chromophore cofactors that absorb light, capturing the energy and using it to split CPDs without cleavage of the DNA backbone or involvement of other proteins. This enzyme opens DNA in two different places when repairing it to its original, undamaged state. It has been hypothesized that the splitting of CPDs is achieved through the energy of electron transfer. The photolyase enzyme 'breaks' DNA at two sites and occurs at one site right after another. This separation between break one and two occurs when an electron travels between the two sites. The enzyme inserts an electron into the CPD, and repairs the first site directly, but instead of taking the straightforward path to the second site, the electron takes the circular path around the CPD. There is another molecule that allows the electron to travel more efficiently to the second site, making the indirect pathway more efficient. Topical application of the photolyase lotion reduced the number of UVB-induced cyclobutane dimers by 45% and prevented UVB-induced immunosuppressive effects. In addition, photolyase can prevent erythema and "sunburn" cell formation. Furthermore, CPD repair by photolyase results in upregulation of cytokine-induced intercellular adhesion molecule-1 (ICAM-1) expression in keratinocytes. ICAM-1 stabilizes cell-to-cell interactions and facilitates leukocyte endothelial transmigration. Lastly, photolyase is "photoreactive", meaning that it requires light in order to be activated; therefore it can be a useful adjunct to sunscreens. The visible blue light hits the photolyase and triggers two photoreceptor molecules: FADH and MTHF. These molecules both have the ability to transfer electrons, which is attributed to a theory that photolyases work by the mechanism of electron transfer.

Supplement—Combination Therapy

In some embodiments, the DNA repair composition is in an oral formulation and can be combined with dietary supplement compositions containing one or more of resveratrol material, carotenoid material, nicotinamide material, DMAE material, zinc source material, and qjuinic acid-containing material, where no other known bioactive nutrient agents having competing modes of action to these specified agents are intentionally excluded from mixtures containing at least two of these DNA repair enhancing ingredients. The compositions may be embodied in formulations for oral administration, or alternatively, in formulations for peritoneal, rectal, intravenous, intramuscular, subcutaneous, or other routes of administration. The combined composition may be selected from the group consisting of resveratrol (3,5,4'-trihydroxy-stilbene or an equivalent polyphenol in pure chemical form); the carotenoid material may be alpha carotene, beta carotene, canthaxanthin, lycopene and mixtures thereof, the nicotinamide material may be selected from the group consisting of nicotinamide, niacin, and mixtures thereof; the DMAE material selected from a group consisting of other choline analogs that pass the blood brain barrier; the zinc source material may be one or more zinc salts; and the quinic acid-containing material selected from a group consisting of quinic acid compounds that can enhance DNA repair by enhancing the uptake of tryptophan and nicotinamide ingredients. For human administration, the resveratrol material, carotenoid material, nicotinamide material, zinc source material, DMAE material, and quinic acid material may be present in proportions effective, in combination, to improve resistance to DNA damage, enhance DNA repair capacity, and stimulate immune function in a human subject to whom the composition is administered as a daily dosage. In some embodiments, the DNA repair composition could include one or more antibiotics (e.g., an antibacterial, antiviral, antifungal, or antiparasitic agent). Not to be limited by theory, but the administration of an antibiotic together with a DNA repair composition may synergistically treat conditions such as bacterial overgrowth, inflammatory bowel disease, *Clostridium difficile* and other forms of colitis, *Helicobacter pylori* and other forms of gastritis, and other conditions. In some embodiments, the DNA repair composition could be combined with an anti-ulcer agent such as an H2 blocker, proton pump inhibitor, sucralfate, bismuth subsalicylate, octreotide, or another agent. In some embodiments, the DNA repair composition could be combined with an anti-inflammatory agent such as 5-ASA and other NSAIDs, a corticosteroid, and the like. In some embodiments, the DNA repair composition could be combined with a chemotherapeutic agent such as, for example, 5-FU, fludarabine, methotrexate, mycophenolate, curcurmin, thalidomide, leflunatnide, an endothelial or fibrous tissue growth factors or neutrotrophic growth proteions can also be incorporated.

In some embodiments, the DNA repair composition and the supplement composition, or other composition can be administered either together in the same formulation, or administered in separate formulations.

Methods of Treatment

An individual suffering from a disease or disorder, or wishing to be treated to prevent a disease or disorder may be treated using compositions as described herein. By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated. As such, treatment includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of individuals are treatable according to the subject methods. Generally such individuals are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the individuals will be humans. In certain embodiments, the methods of treatment involve administration of an effective amount of a compound that creates a desired therapeutic activity.

The DNA repair enzymes may be administered using any convenient protocol capable of resulting in the desired therapeutic activity. Thus, the agent can be incorporated into a variety of formulations for therapeutic administration. More particularly, agents as disclosed herein can be formulated into pharmaceutical or neutraceutical compositions by combination with appropriate, pharmaceutically acceptable carriers or diluents (Remington: The Science and Practice of Pharmacy, 19th Edition, Alfonso, R., ed., Mack Publishing Co. (Easton, Pa. 1995)), and may be formulated into preparations in solid, semi-solid, liquid or gaseous forms, such as tablets, capsules, powders, granules, ointments, solutions, suppositories, injections, inhalants and aerosols. In some embodiments where the DNA repair enzyme is part of a neutraceutical composition, the composition could be in the form of, for example, a tablet, a powder, or a liquid (such as a sports or other drink).

In some embodiments, DNA repair enzymes can also be administered by inhalation. Commercially available nebulizers for liquid formulations, including jet nebulizers and ultrasonic nebulizers are useful for such administration. In some embodiments, the DNA repair enzymes can also be aerosolized using a fluorocarbon formulation and a metered dose inhaler, or inhaled as a lyophilized and milled powder.

The DNA repair enzymes may be placed into a container with a sterile access port, for example, an intravenous solution bag or vial having a stopper pierceable by a hypodermic injection needle.

In pharmaceutical dosage forms, the DNA repair enzymes or other compounds may be used alone or in appropriate association, as well as in combination with other pharmaceutically active or inactive compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories or enemas by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Each dosage for human and animal subjects will preferably contain a predetermined quantity of compounds calculated in an amount sufficient to produce the desired effect, in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, antioxidants, low molecular weight (less than about 10 residues) polypeptides, tonicity adjusting agents, stabilizers, wetting agents and the like, are readily available to the public. "Carriers" when used herein refers to pharmaceutically acceptable carriers, excipients or stabilizers which are nontoxic to the cell or mammal being exposed to the carrier at the dosages and concentrations used.

Administration of the agents can be achieved in various ways, including intracranial, either injected directly into the brain tissue or injected into the cerebrospinal fluid, oral, buccal, rectal, parenteral, intraperitoneal, intradermal, transdermal, intracheal, intracerebral, etc., administration. The antibodies may be administered in combination with one or more additional therapeutic agents. Administration may be chronic or intermittent, as deemed appropriate by the supervising practitioner, particularly in view of any change in the disease state or any undesirable side effects. Administration "in combination with" one or more further therapeutic agents includes both simultaneous (at the same time) and consecutive administration in any order. "Chronic" administration refers to administration of the agent in a continuous manner while "intermittent" administration refers to treatment that is not done without interruption.

In some embodiments, as a convenient form of dietary supplement, the supplement compositions described above are provided in the form of tablet. However, it should be understood that tablet is only one of various convenient dosage forms which can be used for the supplement composition. Other suitable forms include hard or soft-gelatin capsules, powders, or in liquid dosage forms, such as elixirs, syrups, dispersed powders or granules, emulsions, or aqueous or oily suspensions. When other dosage forms are used, the amounts of the active components in one dosage can remain the same, however, the concentration of the component in different pharmaceutical media can be different.

In some embodiments, the supplement composition is formulated as a tablet, and as such it can contain pharmaceutically acceptable excipients, according to methods and procedures well known in the art. As used herein, "excipients" means substances that are of little or no therapeutic value, but useful in the manufacture and compounding of various pharmaceutical preparations, which form the medium of the supplement composition. These substances include coloring, flavoring, and diluting agents; emulsifying and suspending agents; ointment bases; pharmaceutical solvents; antioxidants and preservatives for the product; and miscellaneous agents. Suitable excipients are described in Remington's Pharmaceutical Sciences, Mack Publishing Company, a standard reference text in this field, which is incorporated herein by reference in its entirety.

As used herein, "tablets" are solid pharmaceutical dosage forms containing active ingredients with or without suitable diluents and prepared either by compression or molding methods well known in the art. Although tablets are most frequently discoid in shape, they may also be round, oval, oblong, cylindrical, or triangular. They may differ greatly in size and weight depending on the amount of active ingredients present and the intended method of administration. They are divided into two general classes, (1) compressed tablets, and (2) molded tablets or tablet triturates. In addition to the active ingredients, tablets contain a number of inert excipients or additives. A first group of such excipients includes those materials that help to impart satisfactory compression characteristics to the formulation, including diluents, binders, and lubricants. A second group of such excipients helps to give additional desirable physical characteristics to the finished tablet, such as disintegrators, colors, flavors, and sweetening agents. Compressed tablets can be uncoated or can be sugar coated or film coated by known techniques to mask any unpleasant taste and protect the tablet from the atmosphere, or enteric coated for selective disintegration and adsorption in the gastrointestinal tract.

As used herein, "diluents" are inert substances added to increase the bulk of the formulation to make the tablet a practical size for compression. Commonly used diluents include calcium phosphate, calcium sulfate, lactose, kaolin, mannitol, sodium chloride, dry starch, powdered sugar, silica, and other suitable materials. As used herein, "binders" are agents used to impart cohesive qualities to the powdered material. Binders insure the tablet remaining intact after compression, as well as improving the free-flowing, qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and other suitable materials. As used herein, "lubricants" are materials that perform a number of functions in tablet manufacture, such as improving the rate of flow of the tablet granulation, preventing adhesion of the tablet material to the surface of the dies and punches, reducing interparticle friction, and facilitating the ejection of the tablets from the die cavity. Commonly used lubricants include talc, magnesium stearate, calcium stearate, stearic acid, and hydrogenated vegetable oils. As used herein, "coloring agents" are chemicals that give tablets a more pleasing appearance, and in addition help the manufacturer to control the product during its preparation and help the user to identify the product. Any of the approved certified water-soluble FD&C dyes, mixtures thereof, can be used to color tablets.

An effective amount of a compound to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Typically, the patient may take a DNA repair composition until a dosage is reached that provides the required biological effect.

Treatment Locations

In some embodiments, the DNA repair enzyme preparation can have a local effect, a systemic effect, or both. With regard to local effects, the DNA repair enzyme could prevent or treat a condition of the eyes via an ophthalmic preparation, to treat conditions such as glaucoma, optic neuritis, retinopathy, cataracts, macular degeneration, corneal abrasions or ulcers, melanomas, basal cell carcinomas, and other malignant or benign tumors.

In some embodiments, a DNA repair enzyme nasal preparation, such as a nasal spray could treat a nasal condition such as rhinitis, sinusitis, polyps, ulcers, infection, or benign or malignant tumors.

In some embodiments, a DNA repair aerosolized formulation could treat a condition of the airway or the lungs such as asthma, bronchitis, COPD, bronchiectasis, cystic fibrosis, pneumonia, polyps, interstitial lung disease, Churg-Strauss, tuberculosis, an autoimmune condition, or lung carcinoma for example.

Figure 7:
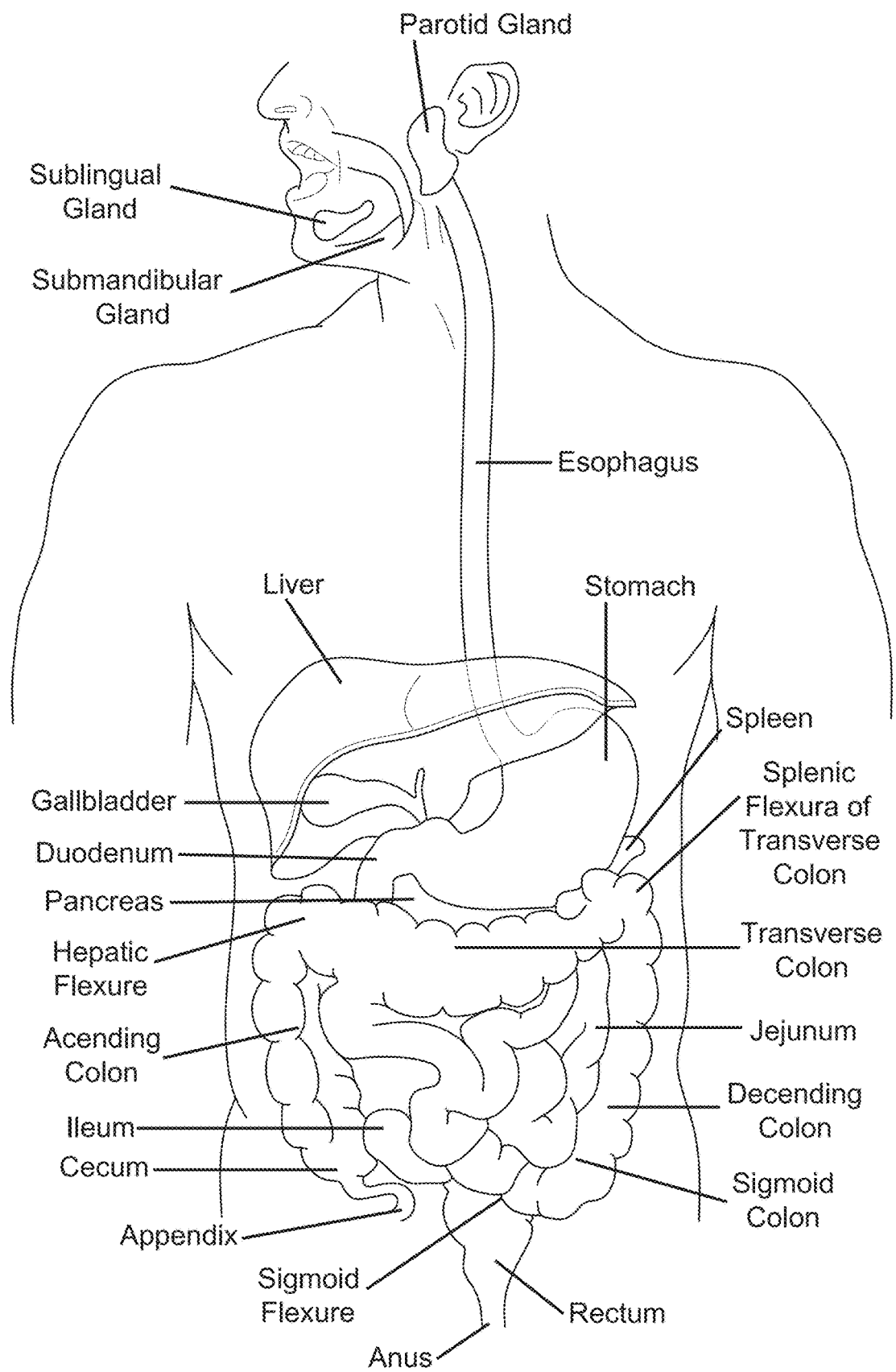
FIG. 7 illustrates certain non-limiting treatment locations for a DNA repair enzyme preparation, according to some embodiments of the invention.

FIG. 7 illustrates certain non-limiting treatment locations for a DNA repair enzyme preparation, according to some embodiments of the invention. In some embodiments, a DNA repair enzyme oral preparation, such as a mouthwash, could treat an intraoral condition such as ulcers, polyps, dental caries or other dental conditions, gingivitis or other gum conditions, infections, including oral candidiasis, cold sores, canker sores, and the like.

In some embodiments, a DNA repair enzyme oral preparation could treat an esophageal condition, such as esophagitis, Barrett's esophagus, an infection such as candidiasis, bacterial, or viral infections, ulcers, polyps, or benign or malignant tumors. The preparation could be in a pill or a non-pill formulation such as a slurry, gel, or other formulation that can increase surface area coverage across the esophageal mucosa.

In some embodiments, a DNA repair enzyme oral preparation could treat gastric conditions such as gastritis, peptic ulcer disease, polyps, or benign or malignant tumors.

In some embodiments, a DNA repair enzyme oral preparation could treat a condition of the small intestine, e.g., within the duodenum, jejunum, and/or ileum. The DNA repair enzyme oral preparation could treat a condition of the large intestine, e.g., within the ascending, transverse, or descending colon. The condition could be an ulcer, enteritis, abscess, inflammatory bowel disease, including Crohn's disease or ulcerative colitis, or other conditions such as celiac sprue, ischemic bowel, diverticulitis, or diverticulosis. A DNA repair enzyme rectal preparation could treat a condition of the rectum or anus, such as proctitis, ulcers, hemorrhoids, abscess, fistula, dysplasia, warts, or other benign or malignant tumors.

For delivery of the DNA repair enzyme composition to an anatomical location distal to the stomach (for example, to treat inflammatory bowel disease), it can be desirable to utilize a modified-release drug delivery system specifically configured for release into the small or large intestine, to avoid inactivation by the stomach. For example, a pH-dependent enteric coating which dissolves at a selected pH value, e.g., greater than 7, may be used. U.S. Pat. No. 5,840,332 describes a GI delivery system that achieves the desired location of release of an agent in the intestine through the inclusion of particulate water-insoluble material embedded in a water-insoluble coating on a drug-containing core. U.S. Pat. No. 6,004,581 describes a multiparticulate spherical-granule-containing formulation that provides for a modified and targeted release of an agent, particularly to the small and large bowel.

Other approaches rely on a pH-dependent coating to achieve the desired release. For example, an enteric-coated commercial product, ASACOL™, relies on a pH-dependent acrylic-based barrier coating, which dissolves at pH values above 7, to achieve a distal 5-ASA delivery. Other examples of this type of formulation are described in U.S. Pat. Nos. 5,541,170 and 5,541,171, which describe a solid dosage form of 5-ASA, or its salts or esters, that achieves delivery to the large intestine through a coating that is insoluble in gastric and intestinal conditions (less than pH 7) but soluble in the colon (pH greater than 7).

U.S. Pat. No. 5,716,648 describes an oral composition that relies on a dependent soluble coating, but also includes a pH-regulating alkaline material to attempt to compensate for patients with "subnormal intestinal pH." Other approaches include those described in U.S. Pat. No. 5,866,619, which is generally directed to a non-pH-dependent colonic drug-delivery system involving a saccharide-containing polymer, which is enzymatically degraded by the colon. Another example is provided by U.S. Pat. No. 6,506,407, which generally describes a colon-specific drug-releasing system that combines a pH-dependent outer coating with the inclusion of a saccharide substrate, which upon enzymatic breakdown by enterobacteria produces an organic acid that subsequently dissolves an acid-soluble inner coating.

Still other examples are described in U.S. Pat. Pub. No. 2002/0098235, which describes the use of multiple pH-dependent coatings to reduce the impact of coating fractures. U.S. Pat. Pub. No. 2001/0055616 describes a pellet formulation for treating intestinal tract conditions, which utilizes a pH-dependent enteric coating to target release from a non-gel-forming drug-containing polymeric matrix core. U.S. Application 2001/0036473 describes a pH-dependent coating on a hydroxypropyltnethylcellulose capsule for enteric and colonic delivery, U.S. Pat. Pub. No. 2001/0026807 describes various coatings, including pH-dependent materials, redox-sensitive materials, and materials subject to breakdown by bacteria, on a starch capsule to achieve colonic delivery.

In some embodiments, the DNA repair enzyme could be complexed to a medical device, such as a stent, sleeve, balloon, probe, capsule, or other device for temporary or permanent implantation into a body region for either targeted and/or long-acting drug delivery. In some embodiments, the medical device is at least partially biodegradable. In some embodiments, the DNA repair formulation is delivered to a desired region of the body via an endoscope or laparoscope, such as during an EGD, colonoscopy, sigmoidoscopy, or anoscopy for example.

The pertinent portions of every cited publication or references are incorporated herein by reference. While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope. Although certain embodiments and examples are disclosed above, inventive subject matter extends beyond the specifically disclosed embodiments to other alternative embodiments and/or uses and to modifications and equivalents thereof. Thus, the scope of the claims appended hereto is not limited by any of the particular embodiments described. For example, in any method or process disclosed herein, the acts or operations of the method or process can be performed in any suitable sequence and are not necessarily limited to any particular disclosed sequence. Various operations can be described as multiple discrete operations in turn, in a manner that can be helpfid in understanding certain embodiments; however, the order of description should not be construed to imply that these operations are order dependent. Additionally, the structures, systems, and/or devices described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein. Thus, the invention is limited only by the claims that follow.

What is claimed is:

1. A skin care composition, comprising:
   an epidermal growth factor (EGF), wherein the EGF is derived from transgenic barley;
   a DNA repair enzyme encapsulated by a liposome comprising a therapeutically effective amount of T4 endonuclease;
   nicotinamide;
   at least one of hydroquinone or kojic acid; and
   at least one of: zinc or green tea extract.

2. The skin care composition of claim 1, wherein the composition is therapeutically effective to improve the appearance of under eye bags.

3. The skin care composition of claim 1, wherein the DNA repair enzyme is encapsulated by a liposome comprising up to 1% by weight of *Micrococcus* lysate.

4. The skin care composition of claim 1, wherein the skin care composition also comprises up to 5% by weight of *Hibiscus Abelmoschus* extract.

5. The skin care composition of claim 1, wherein the skin care composition also comprises 1% by weight of a *Brassica Camprestris* compound.

6. The skin care composition of claim 1, wherein the skin care composition also comprises up to 5% by weight of Alba flower extract.

7. The skin care composition of claim 1, wherein the skin care composition comprises up to 1% of a *Salicornia Herbacea* extract, and a therapeutically effective amount of rapeseed sterol and nonapeptide-1.

8. The skin care composition of claim 1, wherein the skin care composition comprises up to 1% by weight of *Epilobium Angustifolium* extract, up to 1% by weight of Spanish lavender extract; up to 1% of beta glucan, up to 1% by weight of plankton extract, up to 1% by weight of *Arabidopsis Thaliana* extract, up to 1% by weight of *Rosemarinus Officinalis* extract, up to 1% by weight of *Gardenia Taitensis* flower extract, and a therapeutically effective amount of hyaluronic acid, willowherb, mattixyl 3000, and tetrapeptide.

9. The skin care composition of claim 1, wherein the skin care composition comprises up to 5% by weight of *Hibiscus Abelmoschus* extract, up to 1% by weight of a *Brassica Camprestris* compound, up to 5% by weight of Alba flower extract, up to 1% of a *Salicornia Herbacea* extract, and a therapeutically effective amount of rapeseed sterol and nonapeptide-1.

10. The skin care composition of claim 1, wherein the EGF is present in the composition in a concentration of between 1 ppm and 50 ppm.

11. The skin care composition of claim 1, wherein the DNA repair enzyme also comprises a photolyase.

12. The skin care composition of claim 1, wherein the DNA repair enzyme also comprises OGG-1.

* * * * *